(12) United States Patent
Tryggvason et al.

(10) Patent No.: US 6,207,811 B1
(45) Date of Patent: Mar. 27, 2001

(54) NEPHRIN GENE AND PROTEIN

(76) Inventors: Karl Tryggvason, Lokevägen 8 A S-182 61, Djursholm (SE); Marjo Kestila; Ulla Lenkkeri, both of University of Oulu, Biocenter and Department of Biochemistry, Linnanma 90570 Oulu (FI); Minna Mannikko, Jefferson Medical College Department of Dermatology 233 S. 10$^{th}$ St., Rm 450 BLSB, Philadelphia, PA (US) 19107

( * ) Notice: Subject to any disclaimer, the term of this patent is extended or adjusted under 35 U.S.C. 154(b) by 0 days.

(21) Appl. No.: 09/040,774

(22) Filed: Mar. 18, 1998

(51) Int. Cl.$^7$ ............ C07H 21/02; C07H 21/04; C12Q 1/68

(52) U.S. Cl. .......... 536/23.1; 536/22.1; 536/24.3; 536/24.31; 536/24.32; 536/24.33; 435/6; 435/91.2; 435/810

(58) Field of Search ............... 536/22.1, 23.1, 536/24.3, 24.31, 24.32, 24.33; 435/6, 91.2, 810

(56) References Cited

PUBLICATIONS

Altschul, S. F., Gish, W., Miller, W., Myers, E. W., and Lipman, D.J. (1990) Basic local alignment search tool. J. Mol. Biol. 215, 403–10.

Appel R.D., Bairoch, A. and Hochstrasser, D.F. (1994) A new generation of information retrieval tools for biologists: the example of the ExPASy WWW server. Trends Biochem. Sci. 19:258–260.

Barker, D., Hostikka, S.L., Zhou, J., Chow, L.T., Oliphant, A.R., Gerken, S.C., Gregory, M.C., Skolnick, M.H., Atkin, C.L. and Tryggvason, K. (1990) Identification of mutations in the COL4A5 collagen gene in Alport syndrome. Science 248, 1224–1227.

Brümmendott, T., and Rathjen, F.G. (1994) Cell adhesion molecules 1: Immunoglobulin superfamily. Protein profile 1, 951–1058.

Burge, C. and Karlin, S. (1997) Prediction of complete gene structures in human genomic DNA. J. Mol. Biol. 268, 78–94.

de la Chapelle, A. (1993) Disease gene mapping in isolated human populations: the example of Finland. J. Med. Genet. 30:857–865.

Dolan, M., Horchar, T., Rigatti, B., and Hassell, J.R. (1997) Identification of sites in domain I perlecan that regulate heparan sulfate synthesis. J. Biol. Chem. 272, 4316–4322.

Fahrig, T., Landa, C., Pesheva, P., Kühn, K., and Schacher, M. (1987) Characterization of binding properties of the myelin–associated glycoprotein to extracellular matrix constituents. EMBO J. 6, 2875–2883.

Fuchhuber, A., Niaudet, P., Gribouval, O., Genevieve, J., Gubler, M–C., Broyer, M. and Antignac, C. (1996) Congenital nephrotic syndrome of the Finnish type: linkage to the locus in a non–Finnish population. Pediatr. Nephrol. 10: 135–138.

Hästbacka, J., de la Chapelle, A., Mahtani, M.M., Clines, G., Reeve–Daly, M.P., Daly, M., Hamilton, B.A., Kusumi, K., Trivedi, B., Weaver, A., Coloma, A., Lovett, M., Buckler, A., Kaitila, I., and Lander, E.S. (1994) The diastrophic dysplasia gene encodes a novel sulfate transporter: positional cloning by fine–structure linkage disequilibrium mapping. Cell 78, 1073–1087.

Holmberg, C., Antikainen, M., Rönnholm, K., Ala–Houhala, M. and Jalanko, H. (1995) Management of congenital nephrotic syndrome of the Finnish type. Pediatr. Nephrol. 9: 87–93.

Ikonen, E., Baumann, M., Grön, K., Syvänen, A–C., Enomaa, N., Halila, R., Aula, P. and Peltonen, L. (1991) Aspartylglucosaminuria: cDNA encoding human aspartylglucosaminidase and the missense mutation causing the disease. EMBO J. 10: 51–58.

Jurka, J., Klonowski, P., Dagman, V., Pelton, P. (1996) CENSOR—a program for identification and elimination of repetitive elements from DNA sequences. Computers and Chemistry vol. 20 (No. 1):119–122.

Kallunki, P., and Tryggvason, K. (1992) Human basement membrane heparan sulfate proteoglycan core protein: a 467 kD protein containing multiple domains resembling elements of the low density lipoprotein receptor, laminin, neural cell adhesion molecules, and epidermal growth factor. J. Cell Biol. 116, 559–571.

Kasinath, B.S. and Kanwar, Y.S. (1993) Glomerular basement membrane: biology and physiology. In: Molecular and cellular aspects of basement membranes (D. Rorhbach and R. Timpl, eds), Academic Press, pp. 89–106.

Kawai, S., Nomura, S., Harano, T., Fukushima, T., & Osawa, G.(1996) The COL4A5 gene in Japanese Alport syndrome patients: spectrum of mutations of all exons. Kidney Int. 49, 814–822.

Keino–Masu, K., Masu, M. Hinck, L., Leonardo, E.D., Chan. S.S.Y., Culotti, J.G., and Tessier–Lavigne, M. (1996) Cell 87, 175–185.

(List continued on next page.)

*Primary Examiner*—Jeffrey Fredman
(74) *Attorney, Agent, or Firm*—Fay, Sharpe, Fagan, Minnich & McKee, LLP

(57) ABSTRACT

The present invention provides for compositions and methods for detecting susceptibility for basement membrane disease, in particular Congenital nephrotic syndromes of the Finnish type. The present invention provides for nucleic acids and protein for use in methods and compositions for the diagnosis of disease and identification of small molecule therapeutics for treatment of such disease, in particular of proteinuria associated with kidney disease.

4 Claims, 7 Drawing Sheets

OTHER PUBLICATIONS

Kestilä, M., Männikkö, M., Holmberg, C., Korpela, K., Savolainen, E.R., Peltonen, L. and Tryggvason, K. (1994a) Exclusion of eight genes as mutated loci in congenital nephrotic syndrome of the Finnish type. Kidney Int. 45, 986–990.

Kestilä, M., Männikkö, M., Holmberg, C., Gyapay, G., Weissenbcah, J., Savolainen, E.R., Peltonen, L. and Tryggvason, K. (1994b) Congenital nephrotic syndrome of the Finnish type maps t the long arm of chromosome 19. Am. J. Hum. Genet. 54, 757–764.

Knebelmann, B., Breillat, C., Forestier, L., Arrondel, C., Jacassier, D., et al. (1996) Spectrum of mutations in the COL4A5 collagen gene in X–linked Alport syndrome. Am. J., Hum. Genet. 59, 1221–1232.

Koskimies, O. (1990) Genetics of congenital and early infantile nephrotic syndromes. In: Spitzer, A., Avner, E.D. (eds) Inheritance of kidney and uritary tract diseases. Kluwer, Boston, Dordrecht and London, p. 131–138.

Laine, J., Jalanko, H., Holthöfer, H., Krogerus, L., Rappola, J., von Willebrand, E., Lautenschlager, I., Salmela, K. and Holmberg, C. (1993) Post–transplantation nephrosis in congenital nephrotic syndrome of the Finnish type. Kidney Int. 44: 867–874.

Ljungberg, P., Jalanko, H., Holmberg, C. and Holthöfer, H. (1993) Congenital nephrosis of the Finnish type (CNF): matrix components of the glomerular basement membranes and of cultured mesangial cells. Histochem. J. 25:606–612.

Mahan, J.D., Mauer, S.M. Sibley, R.K. and Vernier, R.L. (1984) Congenital nephrotic syndrome: Evolution of medical management and results of renal transplantation. J. Pediatr. 105: 549–557.

Männikkö, M., Kestilä, M., Holmberg, C., Norio, R., Ryynänen, M., Olsen, A., Peltonen, L. and Tryggvason, K. (1995) Fine mapping and haplotype analysis of the locus for congenital nephrotic syndrome on chromosome 19q13.1 Am. J. Hum. Genet. 57:1377–1383.

Männikkö, Kestilä, M., Lenkkeri, U., Alakurtti, H., Holmberg, C., Leisti, J., Salonen, R., Aula, P., Mustonen, A., Peltonen, L. and Tryggvason, K. (1997) Improved prenatal diagnosis of the congenital nehprotic syndrome of the Finnish type nased on DNA analysis, Kidney Int. 51: 868–872.

Noonan, D. M., Fulle, A., Valente, P., Cai, S., Horigan, E., Sasaki, M., Yamada, Y., and Hassell, J.R. (1991) The complete sequence of perlecan, a basement membrane heparan sulfate proteoglycan, reveals extensive similarity with laminin A chain, low density lipoprotein receptor, and the neural cell adhesion molecule. J. Biol. Chem. 266, 22929–22947.

Olsen, A., Georgescu, A. Johnson, S. and Carrano, A. V. (1996) Assembly of a 1–Mb restriction–mapped cosmid contig spanning the candidate region for Finnish congenital nephrosis (NPHS1) in 19q13.1 Genomics 34:223–225.

Pesheva, P., Gennarini, G., Goridis, C., and Schacher, M. (1993) the F3/11 cell adhesion molecule mediates the repulsion of neurons by the extracellular matrix glycoprotein J1–160/180. Neuron 10, 69–82.

Rapola, J., Huttunen, N.P. and Hallman, N. (1992) Congenital and infantile nephrotic syndrome. In: Edelman CM (ed.) Pediatric Kidney Disease. $2^{nd}$ ed. Little, Brown and Company, Boston. vol. 2: 1291–1305.

Renieri, A., Bruttini, M., Galli, L., Zanell, P., Neri, T., et al. (1996) X–linked Alport syndrome: an SSCP–based mutation survey over all 51 exons of the COL4A5 gene. Am. J. Hum. Genet. 58, 1192–1204.

Solovyev, V.V., Salamov, A.A., Lawrence, C.B. (1994) Predicting internal exons by oligonucleotide composition and discriminant analysis of spliceable open reading frames. Nucl. Acids Res. 22(24): 5156–5163.

Tryggvason, K. (1996) Mutations in type IV collagen genes in Alport syndrome. In: Molecular pathology and Genetics of Alport syndrome (ed. K. Tryggvason). Contrib. Nephrol., 117, 154–171, Karger, Basel.

Tryggvason, K. and Kouvalainen, K. (1975) Number of nephrons in normal human kidneys and kidneys of patients with the congenital nephrotic syndrome. Nephron 15: 62–68.

Uberbacher, E.C. and Mural, R.J. (1991) Locating protein––coding regions in human DNA sequences by a multiple sensor–neural network approach, Proc. Natl. Acad. Sci. USA 88: 11261–11265.

Zisch, A.H., D'Allessandri, L., Ranscht, B., Falchetto, R., Winterhalter, K.H., and Vaughan, L. (1992) Neuronal cell adhesion molecule contactin/F11 binds to tenascin via its immunoglobulin–like domains. J. Cell Biol. 119, 203–213.

Kestila, M., et al. "Positionally Cloned Gene for a novel Glomerular Protein (Nephrin) is Mutated in Congenital Nephrotic Syndrome," Molecular Cell, vol. 1, No. 4, Mar. 1998, pp. 575–582.

Lamerden, J.E., et al., "Sequence Analysis of a 1Mb Region in 19q13.1," EMBL Sequence Database, Jul. 11, 1997.

Olsen, A.S., et al., "Assembly of a 10Mb Restriction––Mapped Cosmid Contig Spanning the Candidate Region for Finnish Congenital Nephrosis (NPHS1) in 19Q13.1," Genomics, vol. 34, No. 2, Jun. 1, 1996, pp. 223–225.

Lenkkeri, U., et al., "Structure of the Gene for Congenital Nephrotic Syndrome of the Finnish Type (NPHS1) and Characterization of Mutations," American journal of Human Genetics, vol. 64, No. 1, Jan. 1999, pp. 51–56.

Hiller et al, "WashU—NCI human EST project", Genbank Locus AA678622, Dec. 1997.*

Lamerdin et al, "Sequence analysis of a 1 mb region in human 19q13.1", Genbank Locus HSU95090, Oct. 1997.*

Stratagene catalog, p. 39, 1988.*

* cited by examiner

```
   1  MALGTTLRAS LLLLGLLTEG L↓QLAIPASV PRGFWALPEN LTVVEGASVE
  51  LRCGVSTPGS AVQWAKDGLL LGPDPRIPGF PRYRLEGDPA RGEFHLHIEA
 101  CDLSDDAEYE CQVGRSEMGP ELVSPRVILS ILVPPKLLLL TPEAGTMVTW
 151  VAGQEYVVNC VSGDAKPAPD ITILLSGQTI SDISANVNEG SQQKLFTVEA
 201  TARVTPRSSD NRQLLVCEAS SPALEAPIKA SFTVNVLFPP GPPVIEWPGL
 251  DEGHVRAGQS LELPCVARGG NPLATLQWLK NGQPVSTAWG TEHTQAVARS
 301  VLVMTVRPED HGAQLSCEAH NSVSAGTQEH GITLQVTFPP SAIIILGSAS
 351  QTENKNVTLS CVSKSSRPRV LLRWWLGWRQ LLPMEETVMD GLHGGHISMS
 401  NLTFLARRED NGLTLTCEAF SEAFTKETFK KSLILNVKYP AQKLWIEGPP
 451  EGQKLRAGTR VRLVCLAIGG NPEPSLMWYK DSRTVTESRL PQESRRVHLG
 501  SVEKSGSTFS RELVLVTGPS DNQAKFTCKA GQLSASTQLA VQFPPTNVTI
 551  LANASALREG DALNLTCVSV SSNPPVNLSW DKEGERLEGV AAPPRRAPFK
 601  GSAAARSVLL QVSSRDHGQR VTCRAHSAEL RETVSSFYRL NVLYRPEFLG
 651  EQVLVVTAVE QGEALLPVSV SANPAPEAFN WTFRGYRLSP AGGPRHRILS
 701  SGALHLWNVT RADDGLYQLH CQNSEGTAEA RLRLDVHYAP TIRALQDPTE
 751  VNVGGSVDIV CTVDANPILP GMFNWERLGE DEEDQSLDDM EKISRGPTGR
 801  LRIHHAKLAQ AGAYQCIVDN GVAPPARRLL RLVVRFAPQV EHPTPLTKVA
 851  AAGDSTSSAT LHCRARGVPN IVFTWTKNGV PLDLQDPRYT EHTYHQGGVH
 901  SSLLTIANVS AAQDYALFTC TATNALGSDQ TNIQLVSISR PDPPSGLKVV
 951  SLTPHSVGLE WKPGFDGGLP QRFCIRYEAL GTPGFHYVDV VPPQATTFTL
1001  TGLQPSTRYR VWLLASNALG DSGLADKGTQ LPITTPGLHQ PSGEPEDQLP
1051  TEPPSGPSGL PLLPVLFALG GLLLLSNASC VGGVLWQRRL RRLAEGISEK
1101  TEAGSEEDRV RNEYEESQWT GERDTQSSTV STTEAEPYYR SLRDFSPQLP
1151  PTQEEVSYSR GFTGEDEDMA FPGHLYDEVE RTYPPSGAWG PLYDEVQMGP
1201  WDLHWPEDTY QDPRGIYDQV AGDLDTLEPD SLPFELRGHL V
```

FIG. 4A

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 4285 base pairs
        (B) TYPE: nucleic acid
        (C) STRANDEDNESS: single
        (D) TOPOLOGY: Not Relevant (ii) MOLECULE TYPE: cDNA (ix) FEATURE:
        (A) NAME/KEY: sig_peptide
        (B) LOCATION: 1..66
        (D) OTHER INFORMATION: /note= "putative signal peptide"

(ix) FEATURE:
        (A) NAME/KEY: CDS
        (B) LOCATION: 1..3723

(ix) FEATURE:
        (A) NAME/KEY: mat_peptide
        (B) LOCATION: 67..3723

(ix) FEATURE:
        (A) NAME/KEY: misc_feature
        (B) LOCATION: 121..122
        (D) OTHER INFORMATION: /note= "deletion mutation FIN-Major"

(ix) FEATURE:
      (A) NAME/KEY: misc_feature
      (B) LOCATION: 3800..3804
      (D) OTHER INFORMATION: /note= "nonsense mutation in exon
          26 FIN-Minor"

(ix) FEATURE:
      (A) NAME/KEY: misc_feature
      (B) LOCATION: 3178..3258
      (D) OTHER INFORMATION: /note= "putative transmembrane
          domain"

(xi) SEQUENCE DESCRIPTION: SEQ ID NO:1:

| ATG | GCC | CTG | GGG | ACG | ACG | CTC | AGG | GCT | TCT | CTC | CTG | CTC | CTG | GGG | CTG | 48 |
|---|---|---|---|---|---|---|---|---|---|---|---|---|---|---|---|---|
| Met | Ala | Leu | Gly | Thr | Thr | Leu | Arg | Ala | Ser | Leu | Leu | Leu | Leu | Gly | Leu | |
| -22 | | -20 | | | | -15 | | | | -10 | | | | | | |

| CTG | ACT | GAA | GGC | CTG | GCG | CAG | TTG | GCG | ATT | CCT | GCC | TCC | GTT | CCC | CGG | 96 |
|---|---|---|---|---|---|---|---|---|---|---|---|---|---|---|---|---|
| Leu | Thr | Glu | Gly | Leu | Ala | Gln | Leu | Ala | Ile | Pro | Ala | Ser | Val | Pro | Arg | |
| | -5 | | | | | 1 | | | 5 | | | | | | 10 | |

| GGC | TTC | TGG | GCC | CTG | CCT | GAA | AAC | CTG | ACG | GTG | GTG | GAG | GGG | GCC | TCA | 144 |
|---|---|---|---|---|---|---|---|---|---|---|---|---|---|---|---|---|
| Gly | Phe | Trp | Ala | Leu | Pro | Glu | Asn | Leu | Thr | Val | Val | Glu | Gly | Ala | Ser | |
| | | | | 15 | | | | | 20 | | | | | 25 | | |

| GTG | GAG | CTG | CGT | TGT | GGG | GTC | AGC | ACC | CCT | GGC | AGT | GCG | GTG | CAA | TGG | 192 |
|---|---|---|---|---|---|---|---|---|---|---|---|---|---|---|---|---|
| Val | Glu | Leu | Arg | Cys | Gly | Val | Ser | Thr | Pro | Gly | Ser | Ala | Val | Gln | Trp | |
| | | | 30 | | | | | 35 | | | | | 40 | | | |

| GCC | AAA | GAT | GGG | CTG | CTC | CTG | GGC | CCC | GAC | CCC | AGG | ATC | CCA | GGC | TTC | 240 |
|---|---|---|---|---|---|---|---|---|---|---|---|---|---|---|---|---|
| Ala | Lys | Asp | Gly | Leu | Leu | Leu | Gly | Pro | Asp | Pro | Arg | Ile | Pro | Gly | Phe | |
| | | 45 | | | | | 50 | | | | | 55 | | | | |

| CCG | AGG | TAC | CGC | CTG | GAA | GGG | GAC | CCT | GCT | AGA | GGT | GAA | TTC | CAC | CTG | 288 |
|---|---|---|---|---|---|---|---|---|---|---|---|---|---|---|---|---|
| Pro | Arg | Tyr | Arg | Leu | Glu | Gly | Asp | Pro | Ala | Arg | Gly | Glu | Phe | His | Leu | |
| | 60 | | | | | 65 | | | | | 70 | | | | | |

| CAC | ATC | GAG | GCC | TGT | GAC | CTC | AGC | GAT | GAC | GCG | GAG | TAT | GAG | TGC | CAG | 336 |
|---|---|---|---|---|---|---|---|---|---|---|---|---|---|---|---|---|
| His | Ile | Glu | Ala | Cys | Asp | Leu | Ser | Asp | Asp | Ala | Glu | Tyr | Glu | Cys | Gln | |
| 75 | | | | 80 | | | | | 85 | | | | | 90 | | |

| GTC | GGC | CGC | TCT | GAG | ATG | GGG | CCC | GAG | CTC | GTG | TCT | CCC | AGA | GTG | ATC | 384 |
|---|---|---|---|---|---|---|---|---|---|---|---|---|---|---|---|---|
| Val | Gly | Arg | Ser | Glu | Met | Gly | Pro | Glu | Leu | Val | Ser | Pro | Arg | Val | Ile | |
| | | | | 95 | | | | | 100 | | | | | 105 | | |

| CTC | TCC | ATC | CTG | GTT | CCT | CCC | AAG | CTG | CTC | CTG | CTG | ACC | CCA | GAG | GCA | 432 |
|---|---|---|---|---|---|---|---|---|---|---|---|---|---|---|---|---|
| Leu | Ser | Ile | Leu | Val | Pro | Pro | Lys | Leu | Leu | Leu | Leu | Thr | Pro | Glu | Ala | |
| | | | 110 | | | | | 115 | | | | | 120 | | | |

| GGC | ACC | ATG | GTC | ACC | TGG | GTA | GCT | GGG | CAG | GAG | TAC | GTG | GTC | AAC | TGT | 480 |
|---|---|---|---|---|---|---|---|---|---|---|---|---|---|---|---|---|
| Gly | Thr | Met | Val | Thr | Trp | Val | Ala | Gly | Gln | Glu | Tyr | Val | Val | Asn | Cys | |
| | | 125 | | | | | 130 | | | | | 135 | | | | |

| GTG | TCT | GGG | GAC | GCG | AAG | CCA | GCA | CCT | GAC | ATC | ACC | ATT | CTC | CTG | AGT | 528 |
|---|---|---|---|---|---|---|---|---|---|---|---|---|---|---|---|---|
| Val | Ser | Gly | Asp | Ala | Lys | Pro | Ala | Pro | Asp | Ile | Thr | Ile | Leu | Leu | Ser | |
| | 140 | | | | | 145 | | | | | 150 | | | | | |

| GGA | CAG | ACA | ATA | TCT | GAC | ATC | TCT | GCA | AAC | GTG | AAC | GAG | GGC | TCC | CAG | 576 |
|---|---|---|---|---|---|---|---|---|---|---|---|---|---|---|---|---|
| Gly | Gln | Thr | Ile | Ser | Asp | Ile | Ser | Ala | Asn | Val | Asn | Glu | Gly | Ser | Gln | |
| 155 | | | | | 160 | | | | | 165 | | | | | 170 | |

| CAG | AAA | CTC | TTC | ACT | GTG | GAG | GCC | ACA | GCC | AGG | GTG | ACA | CCC | CGG | AGC | 624 |
|---|---|---|---|---|---|---|---|---|---|---|---|---|---|---|---|---|
| Gln | Lys | Leu | Phe | Thr | Val | Glu | Ala | Thr | Ala | Arg | Val | Thr | Pro | Arg | Ser | |
| | | | | 175 | | | | | 180 | | | | | 185 | | |

| TCA | GAT | AAT | AGG | CAG | TTG | CTG | GTC | TGT | GAG | GCG | TCT | AGC | CCA | GCA | CTG | 672 |
|---|---|---|---|---|---|---|---|---|---|---|---|---|---|---|---|---|
| Ser | Asp | Asn | Arg | Gln | Leu | Leu | Val | Cys | Glu | Ala | Ser | Ser | Pro | Ala | Leu | |
| | | | 190 | | | | | 195 | | | | | 200 | | | |

| GAG | GCC | CCC | ATC | AAG | GCC | TCA | TTC | ACC | GTG | AAT | GTT | CTG | TTC | CCT | CCA | 720 |
|---|---|---|---|---|---|---|---|---|---|---|---|---|---|---|---|---|
| Glu | Ala | Pro | Ile | Lys | Ala | Ser | Phe | Thr | Val | Asn | Val | Leu | Phe | Pro | Pro | |
| | | 205 | | | | | 210 | | | | | 215 | | | | |

| GGA | CCC | CCT | GTC | ATC | GAG | TGG | CCA | GGC | CTG | GAT | GAG | GGG | CAC | GTG | CGG | 768 |
|---|---|---|---|---|---|---|---|---|---|---|---|---|---|---|---|---|
| Gly | Pro | Pro | Val | Ile | Glu | Trp | Pro | Gly | Leu | Asp | Glu | Gly | His | Val | Arg | |
| | 220 | | | | | 225 | | | | | 230 | | | | | |

| | | |
|---|---|---|
| GCA GGA CAG AGC TTG GAG CTG CCG TGC GTG GCC CGA GGG GGT AAT CCC<br>Ala Gly Gln Ser Leu Glu Leu Pro Cys Val Ala Arg Gly Gly Asn Pro<br>235                    240                  245                  250 | 816 |
| TTA GCC ACA CTG CAG TGG CTG AAG AAT GGC CAG CCG GTG TCC ACA GCG<br>Leu Ala Thr Leu Gln Trp Leu Lys Asn Gly Gln Pro Val Ser Thr Ala<br>                  255                  260                  265 | 864 |
| TGG GGC ACA GAG CAC ACC CAG GCG GTG GCC CGC AGT GTG CTG GTG ATG<br>Trp Gly Thr Glu His Thr Gln Ala Val Ala Arg Ser Val Leu Val Met<br>              270                  275                  280 | 912 |
| ACC GTG AGG CCA GAA GAC CAT GGA GCG CAG CTC AGC TGC GAG GCC CAC<br>Thr Val Arg Pro Glu Asp His Gly Ala Gln Leu Ser Cys Glu Ala His<br>            285                  290                  295 | 960 |
| AAC AGC GTG TCT GCA GGG ACC CAG GAG CAC GGC ATC ACA CTG CAG GTC<br>Asn Ser Val Ser Ala Gly Thr Gln Glu His Gly Ile Thr Leu Gln Val<br>        300                  305                  310 | 1008 |
| ACC TTT CCC CCT AGT GCC ATT ATT ATC TTG GGA TCT GCA TCC CAG ACT<br>Thr Phe Pro Pro Ser Ala Ile Ile Ile Leu Gly Ser Ala Ser Gln Thr<br>315                    320                  325                  330 | 1056 |
| GAG AAC AAG AAC GTG ACA CTC TCC TGT GTC AGC AAG TCC AGT CGC CCG<br>Glu Asn Lys Asn Val Thr Leu Ser Cys Val Ser Lys Ser Ser Arg Pro<br>                  335                  340                  345 | 1104 |
| CGG GTT CTG CTA CGA TGG TGG CTG GGC TGG CGG CAG CTG CTG CCC ATG<br>Arg Val Leu Leu Arg Trp Trp Leu Gly Trp Arg Gln Leu Leu Pro Met<br>            350                  355                  360 | 1152 |
| GAG GAG ACA GTC ATG GAT GGA CTG CAT GGC GGT CAC ATC TCC ATG TCC<br>Glu Glu Thr Val Met Asp Gly Leu His Gly Gly His Ile Ser Met Ser<br>            365                  370                  375 | 1200 |
| AAC CTG ACA TTC CTG GCG CGG CGG GAG GAC AAC GGT CTG ACC CTC ACA<br>Asn Leu Thr Phe Leu Ala Arg Arg Glu Asp Asn Gly Leu Thr Leu Thr<br>        380                  385                  390 | 1248 |
| TGT GAG GCC TTC AGT GAA GCC TTC ACC AAG GAG ACC TTC AAG AAG TCG<br>Cys Glu Ala Phe Ser Glu Ala Phe Thr Lys Glu Thr Phe Lys Lys Ser<br>395                    400                  405                  410 | 1296 |
| CTC ATC CTG AAC GTA AAA TAT CCC GCC CAG AAA CTG TGG ATT GAG GGT<br>Leu Ile Leu Asn Val Lys Tyr Pro Ala Gln Lys Leu Trp Ile Glu Gly<br>                  415                  420                  425 | 1344 |
| CCC CCA GAG GGC CAG AAG CTC CGG GCT GGG ACC CGG GTG AGG CTG GTG<br>Pro Pro Glu Gly Gln Lys Leu Arg Ala Gly Thr Arg Val Arg Leu Val<br>            430                  435                  440 | 1392 |
| TGT TTG GCT ATC GGG GGC AAC CCA GAG CCC TCC CTC ATG TGG TAC AAG<br>Cys Leu Ala Ile Gly Gly Asn Pro Glu Pro Ser Leu Met Trp Tyr Lys<br>                  445                  450                  455 | 1440 |
| GAC TCG CGC ACC GTG ACC GAG TCG CGG CTG CCG CAG GAG TCG CGG CGC<br>Asp Ser Arg Thr Val Thr Glu Ser Arg Leu Pro Gln Glu Ser Arg Arg<br>        460                  465                  470 | 1488 |
| GTG CAT CTC GGC AGC GTG GAG AAA TCT GGG AGC ACC TTC TCC CGA GAG<br>Val His Leu Gly Ser Val Glu Lys Ser Gly Ser Thr Phe Ser Arg Glu<br>475                    480                  485                  490 | 1536 |
| CTG GTG CTG GTC ACA GGG CCG TCG GAC AAC CAG GCC AAG TTC ACG TGC<br>Leu Val Leu Val Thr Gly Pro Ser Asp Asn Gln Ala Lys Phe Thr Cys<br>                  495                  500                  505 | 1584 |
| AAG GCT GGA CAG CTC AGC GCG TCC ACG CAG CTG GCG GTG CAG TTT CCC<br>Lys Ala Gly Gln Leu Ser Ala Ser Thr Gln Leu Ala Val Gln Phe Pro<br>            510                  515                  520 | 1632 |
| CCA ACT AAC GTG ACG ATC CTG GCC AAC GCA TCC GCA CTG CGC CCG GGA<br>Pro Thr Asn Val Thr Ile Leu Ala Asn Ala Ser Ala Leu Arg Pro Gly<br>        525                  530                  535 | 1680 |
| GAC GCC TTA AAC TTG ACA TGC GTC AGC GTC AGC AGC AAT CCG CCG GTC<br>Asp Ala Leu Asn Leu Thr Cys Val Ser Val Ser Ser Asn Pro Pro Val | 1728 |

-continued

```
              540                     545                     550
AAC TTG TCC TGG GAC AAG GAA GGG GAG AGG CTG GAG GGC GTG GCC GCC      1776
Asn Leu Ser Trp Asp Lys Glu Gly Glu Arg Leu Glu Gly Val Ala Ala
555                     560                     565                     570

CCA CCC CGG AGA GCC CCA TTC AAA GGC TCC GCC GCC GCC AGG AGC GTC      1824
Pro Pro Arg Arg Ala Pro Phe Lys Gly Ser Ala Ala Ala Arg Ser Val
                    575                     580                     585

CTT CTG CAA GTG TCA TCC CGC GAT CAT GGC CAG CGC GTG ACC TGC CGC      1872
Leu Leu Gln Val Ser Ser Arg Asp His Gly Gln Arg Val Thr Cys Arg
                590                     595                     600

GCC CAC AGC GCC GAG CTC CGC GAA ACC GTG AGC TCC TTC TAT CGC CTC      1920
Ala His Ser Ala Glu Leu Arg Glu Thr Val Ser Ser Phe Tyr Arg Leu
            605                     610                     615

AAC GTA CTG TAC CGT CCA GAG TTC CTG GGG GAG CAG GTG CTG GTG GTG      1968
Asn Val Leu Tyr Arg Pro Glu Phe Leu Gly Glu Gln Val Leu Val Val
        620                     625                     630

ACC GCG GTG GAG CAG GGC GAG GCG TTG CTG CCC GTG TCC GTG TCC GCT      2016
Thr Ala Val Glu Gln Gly Glu Ala Leu Leu Pro Val Ser Val Ser Ala
635                     640                     645                     650

AAC CCC GCC CCC GAG GCC TTC AAC TGG ACC TTC CGC GGC TAT CGC CTC      2064
Asn Pro Ala Pro Glu Ala Phe Asn Trp Thr Phe Arg Gly Tyr Arg Leu
                    655                     660                     665

AGT CCA GCG GGC GGC CCC CGG CAT CGC ATC CTG TCC AGC GGG GCT CTG      2112
Ser Pro Ala Gly Gly Pro Arg His Arg Ile Leu Ser Ser Gly Ala Leu
                670                     675                     680

CAT CTG TGG AAT GTG ACC CGC GCG GAC GAC GGC CTC TAT CAG CTG CAC      2160
His Leu Trp Asn Val Thr Arg Ala Asp Asp Gly Leu Tyr Gln Leu His
            685                     690                     695

TGC CAG AAC TCT GAG GGC ACC GCG GAA GCG CGG CTG CGG CTG GAC GTG      2208
Cys Gln Asn Ser Glu Gly Thr Ala Glu Ala Arg Leu Arg Leu Asp Val
        700                     705                     710

CAC TAT GCT CCC ACC ATC CGT GCC CTC CAG GAC CCC ACT GAG GTG AAC      2256
His Tyr Ala Pro Thr Ile Arg Ala Leu Gln Asp Pro Thr Glu Val Asn
715                     720                     725                     730

GTC GGG GGT TCT GTG GAC ATA GTC TGC ACT GTC GAT GCC AAT CCC ATC      2304
Val Gly Gly Ser Val Asp Ile Val Cys Thr Val Asp Ala Asn Pro Ile
                    735                     740                     745

CTC CCG GGC ATG TTC AAC TGG GAG AGA CTG GGA GAA GAT GAG GAG GAC      2352
Leu Pro Gly Met Phe Asn Trp Glu Arg Leu Gly Glu Asp Glu Glu Asp
                750                     755                     760

CAG AGC CTG GAT GAC ATG GAG AAG ATA TCC AGG GGA CCA ACG GGG CGC      2400
Gln Ser Leu Asp Asp Met Glu Lys Ile Ser Arg Gly Pro Thr Gly Arg
            765                     770                     775

CTG CGG ATT CAC CAT GCC AAA CTG GCC CAG GCT GGC GCT TAC CAG TGC      2448
Leu Arg Ile His His Ala Lys Leu Ala Gln Ala Gly Ala Tyr Gln Cys
        780                     785                     790

ATT GTG GAC AAT GGG GTG GCG CCT CCA GCA CGA CGG CTG CTC CGT CTT      2496
Ile Val Asp Asn Gly Val Ala Pro Pro Ala Arg Arg Leu Leu Arg Leu
795                     800                     805                     810

GTT GTC AGA TTT GCC CCC CAG GTG GAG CAC CCC ACT CCC CTA ACT AAG      2544
Val Val Arg Phe Ala Pro Gln Val Glu His Pro Thr Pro Leu Thr Lys
                    815                     820                     825

GTG GCT GCA GCT GGA GAC AGC ACC AGT TCT GCC ACC CTC CAC TGC CGT      2592
Val Ala Ala Ala Gly Asp Ser Thr Ser Ser Ala Thr Leu His Cys Arg
                830                     835                     840

GCC CGA GGT GTC CCC AAC ATC GTT TTC ACT TGG ACA AAA AAC GGG GTC      2640
Ala Arg Gly Val Pro Asn Ile Val Phe Thr Trp Thr Lys Asn Gly Val
            845                     850                     855

CCT CTG GAT CTC CAA GAT CCC AGG TAC ACG GAG CAC ACA TAC CAC CAG      2688
Pro Leu Asp Leu Gln Asp Pro Arg Tyr Thr Glu His Thr Tyr His Gln
```

```
                                                      -continued

Pro Leu Asp Leu Gln Asp Pro Arg Tyr Thr Glu His Thr Tyr His Gln
    860                 865                 870

GGT GGT GTC CAC AGC AGC CTC CTG ACC ATT GCC AAC GTG TCT GCC GCC    2736
Gly Gly Val His Ser Ser Leu Leu Thr Ile Ala Asn Val Ser Ala Ala
875                 880                 885                 890

CAG GAT TAC GCC CTC TTC ACA TGT ACA GCC ACC AAC GCC CTT GGC TCG    2784
Gln Asp Tyr Ala Leu Phe Thr Cys Thr Ala Thr Asn Ala Leu Gly Ser
                895                 900                 905

GAC CAA ACC AAC ATT CAA CTT GTC AGC ATC AGC CGC CCT GAC CCT CCA    2832
Asp Gln Thr Asn Ile Gln Leu Val Ser Ile Ser Arg Pro Asp Pro Pro
            910                 915                 920

TCA GGA TTA AAG GTT GTG AGT CTG ACC CCA CAC TCC GTG GGG CTG GAG    2880
Ser Gly Leu Lys Val Val Ser Leu Thr Pro His Ser Val Gly Leu Glu
        925                 930                 935

TGG AAG CCT GGC TTT GAT GGG GGC CTG CCA CAG AGG TTC TGC ATC AGG    2928
Trp Lys Pro Gly Phe Asp Gly Gly Leu Pro Gln Arg Phe Cys Ile Arg
    940                 945                 950

TAT GAG GCC CTG GGG ACT CCA GGG TTC CAC TAT GTG GAT GTC GTA CCA    2976
Tyr Glu Ala Leu Gly Thr Pro Gly Phe His Tyr Val Asp Val Val Pro
955                 960                 965                 970

CCC CAG GCC ACC ACC TTC ACG CTG ACT GGT CTA CAG CCT TCT ACA AGA    3024
Pro Gln Ala Thr Thr Phe Thr Leu Thr Gly Leu Gln Pro Ser Thr Arg
                975                 980                 985

TAC AGG GTC TGG CTG CTG GCC AGT AAT GCC TTG GGG GAC AGT GGA CTG    3072
Tyr Arg Val Trp Leu Leu Ala Ser Asn Ala Leu Gly Asp Ser Gly Leu
            990                 995                 1000

GCT GAC AAA GGG ACC CAG CTT CCC ATC ACT ACC CCA GGT CTC CAC CAG    3120
Ala Asp Lys Gly Thr Gln Leu Pro Ile Thr Thr Pro Gly Leu His Gln
        1005                1010                1015

CCT TCT GGA GAA CCT GAA GAC CAG CTG CCC ACA GAG CCA CCT TCA GGA    3168
Pro Ser Gly Glu Pro Glu Asp Gln Leu Pro Thr Glu Pro Pro Ser Gly
    1020                1025                1030

CCC TCG GGG CTG CCC CTG CTG CCT GTG CTG TTC GCT CTT GGG GGG CTT    3216
Pro Ser Gly Leu Pro Leu Leu Pro Val Leu Phe Ala Leu Gly Gly Leu
1035                1040                1045                1050

CTG CTC CTC TCC AAT GCC TCC TGT GTC GGG GGG GTC CTC TGG CAG CGG    3264
Leu Leu Leu Ser Asn Ala Ser Cys Val Gly Gly Val Leu Trp Gln Arg
                1055                1060                1065

AGA CTC AGG CGT CTT GCT GAG GGC ATC TCA GAG AAG ACA GAG GCA GGG    3312
Arg Leu Arg Arg Leu Ala Glu Gly Ile Ser Glu Lys Thr Glu Ala Gly
            1070                1075                1080

TCG GAA GAG GAC CGA GTC AGG AAC GAA TAT GAG GAG AGC CAG TGG ACA    3360
Ser Glu Glu Asp Arg Val Arg Asn Glu Tyr Glu Glu Ser Gln Trp Thr
        1085                1090                1095

GGA GAG CGG GAC ACT CAG AGC TCC ACG GTC AGC ACA ACA GAG GCA GAG    3408
Gly Glu Arg Asp Thr Gln Ser Ser Thr Val Ser Thr Thr Glu Ala Glu
    1100                1105                1110

CCG TAT TAC CGC TCC CTG AGG GAC TTC AGC CCC CAG CTG CCC CCG ACG    3456
Pro Tyr Tyr Arg Ser Leu Arg Asp Phe Ser Pro Gln Leu Pro Pro Thr
1115                1120                1125                1130

CAG GAG GAG GTG TCT TAT TCC CGA GGT TTC ACA GGT GAA GAT GAG GAT    3504
Gln Glu Glu Val Ser Tyr Ser Arg Gly Phe Thr Gly Glu Asp Glu Asp
                1135                1140                1145

ATG GCC TTC CCT GGG CAC TTG TAT GAT GAG GTA GAA AGA ACG TAC CCC    3552
Met Ala Phe Pro Gly His Leu Tyr Asp Glu Val Glu Arg Thr Tyr Pro
            1150                1155                1160

CCG TCT GGA GCC TGG GGA CCC CTC TAC GAT GAA GTG CAG ATG GGA CCC    3600
Pro Ser Gly Ala Trp Gly Pro Leu Tyr Asp Glu Val Gln Met Gly Pro
        1165                1170                1175
```

```
TGG GAC CTC CAC TGG CCT GAA GAC ACA TAT CAG GAT CCA AGA GGA ATC    3648
Trp Asp Leu His Trp Pro Glu Asp Thr Tyr Gln Asp Pro Arg Gly Ile
    1180                1185                1190

TAT GAC CAG GTG GCC GGA GAC TTG GAC ACT CTG GAA CCC GAT TCT CTG    3696
Tyr Asp Gln Val Ala Gly Asp Leu Asp Thr Leu Glu Pro Asp Ser Leu
1195                1200                1205                1210

CCC TTC GAG CTG AGG GGA CAT CTG GTG TAAGAGCCCT CTCAACCCCA           3743
Pro Phe Glu Leu Arg Gly His Leu Val
                1215

TTGTCCTGCA CCTGCAGGAA TTTACACTCC ACTGGTCTCT CTCATTACAG CCTGGGCCGA   3803

GCTGGTTAGG TGAGCTCCAT AAAACCCAAA GGGACTTGGT GTCAGGAGAG GACATGGAGG   3863

GGGCTGAGTG ACAGAGATGG TTCAGCTGGT ACCAGAGTAG AAACAAGGTG CATCCTGGGG   3923

TTGGCTTTAG AAACTAAACT TCTCCAAAAG GACAGGGCAG ATTGTAAACG TCGTCTCAAA   3983

AATGAAATGC TGCCGGGTGC GGTGACTCAC GCCTATAATC CCAGCACTTT GGGAGGCTGA   4043

GGCGGGTGGA TCACCTGAGG TCAGGAGTTC GAGACCAGCC TGGCCAACAT GGTAAAACTC   4103

CATTTCTACT AAAAATATAA AAAATTAGCC AGGAGTAGTG GCGCATGCCT GTAGTCCCAG   4163

CTACTTGGGA GGCTGATGCA TGAGAATTGC TTGAACCCAG GAGGCGGAGG TTGCAGTGAG   4223

CTGAGATCAC GCCACTGCAC TCCAGCCTGG GCGACAGAGC GAGATTCTGT CTCAAAAAAT   4283

AA                                                                 4285
```

(2) INFORMATION FOR SEQ ID NO:2:

(i) SEQUENCE CHARACTERISTICS:
        (A) LENGTH: 1241 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Leu Gly Thr Thr Leu Arg Ala Ser Leu Leu Leu Gly Leu
-22     -20                 -15                 -10

Leu Thr Glu Gly Leu Ala Gln Leu Ala Ile Pro Ala Ser Val Pro Arg
    -5                   1                   5                  10

Gly Phe Trp Ala Leu Pro Glu Asn Leu Thr Val Val Glu Gly Ala Ser
                15                  20                  25

Val Glu Leu Arg Cys Gly Val Ser Thr Pro Gly Ser Ala Val Gln Trp
                30                  35                  40

Ala Lys Asp Gly Leu Leu Leu Gly Pro Asp Pro Arg Ile Pro Gly Phe
                45                  50                  55

Pro Arg Tyr Arg Leu Glu Gly Asp Pro Ala Arg Gly Glu Phe His Leu
            60                  65                  70

His Ile Glu Ala Cys Asp Leu Ser Asp Ala Glu Tyr Glu Cys Gln
75                  80                  85                  90

Val Gly Arg Ser Glu Met Gly Pro Glu Leu Val Ser Pro Arg Val Ile
                95                  100                 105

Leu Ser Ile Leu Val Pro Pro Lys Leu Leu Leu Thr Pro Glu Ala
                110                 115                 120

Gly Thr Met Val Thr Trp Val Ala Gly Gln Glu Tyr Val Val Asn Cys
                125                 130                 135

Val Ser Gly Asp Ala Lys Pro Ala Pro Asp Ile Thr Ile Leu Leu Ser
            140                 145                 150

Gly Gln Thr Ile Ser Asp Ile Ser Ala Asn Val Asn Glu Gly Ser Gln
155                 160                 165                 170
```

-continued

```
Gln Lys Leu Phe Thr Val Glu Ala Thr Ala Arg Val Thr Pro Arg Ser
            175                 180                 185

Ser Asp Asn Arg Gln Leu Leu Val Cys Glu Ala Ser Ser Pro Ala Leu
            190                 195                 200

Glu Ala Pro Ile Lys Ala Ser Phe Thr Val Asn Val Leu Phe Pro Pro
            205                 210                 215

Gly Pro Pro Val Ile Glu Trp Pro Gly Leu Asp Glu Gly His Val Arg
            220                 225                 230

Ala Gly Gln Ser Leu Glu Leu Pro Cys Val Ala Arg Gly Gly Asn Pro
235                 240                 245                 250

Leu Ala Thr Leu Gln Trp Leu Lys Asn Gly Gln Pro Val Ser Thr Ala
                    255                 260                 265

Trp Gly Thr Glu His Thr Gln Ala Val Ala Arg Ser Val Leu Val Met
                    270                 275                 280

Thr Val Arg Pro Glu Asp His Gly Ala Gln Leu Ser Cys Glu Ala His
            285                 290                 295

Asn Ser Val Ser Ala Gly Thr Gln Glu His Gly Ile Thr Leu Gln Val
            300                 305                 310

Thr Phe Pro Pro Ser Ala Ile Ile Ile Leu Gly Ser Ala Ser Gln Thr
315                 320                 325                 330

Glu Asn Lys Asn Val Thr Leu Ser Cys Val Ser Lys Ser Ser Arg Pro
                    335                 340                 345

Arg Val Leu Leu Arg Trp Trp Leu Gly Trp Arg Gln Leu Leu Pro Met
                    350                 355                 360

Glu Glu Thr Val Met Asp Gly Leu His Gly Gly His Ile Ser Met Ser
            365                 370                 375

Asn Leu Thr Phe Leu Ala Arg Arg Glu Asp Asn Gly Leu Thr Leu Thr
            380                 385                 390

Cys Glu Ala Phe Ser Glu Ala Phe Thr Lys Glu Thr Phe Lys Lys Ser
395                 400                 405                 410

Leu Ile Leu Asn Val Lys Tyr Pro Ala Gln Lys Leu Trp Ile Glu Gly
                    415                 420                 425

Pro Pro Glu Gly Gln Lys Leu Arg Ala Gly Thr Arg Val Arg Leu Val
            430                 435                 440

Cys Leu Ala Ile Gly Gly Asn Pro Glu Pro Ser Leu Met Trp Tyr Lys
            445                 450                 455

Asp Ser Arg Thr Val Thr Glu Ser Arg Leu Pro Gln Glu Ser Arg Arg
            460                 465                 470

Val His Leu Gly Ser Val Glu Lys Ser Gly Ser Thr Phe Ser Arg Glu
475                 480                 485                 490

Leu Val Leu Val Thr Gly Pro Ser Asp Asn Gln Ala Lys Phe Thr Cys
                    495                 500                 505

Lys Ala Gly Gln Leu Ser Ala Ser Thr Gln Leu Ala Val Gln Phe Pro
            510                 515                 520

Pro Thr Asn Val Thr Ile Leu Ala Asn Ala Ser Ala Leu Arg Pro Gly
            525                 530                 535

Asp Ala Leu Asn Leu Thr Cys Val Ser Val Ser Ser Asn Pro Pro Val
            540                 545                 550

Asn Leu Ser Trp Asp Lys Glu Gly Glu Arg Leu Glu Gly Val Ala Ala
555                 560                 565                 570

Pro Pro Arg Arg Ala Pro Phe Lys Gly Ser Ala Ala Arg Ser Val
                    575                 580                 585
```

```
Leu Leu Gln Val Ser Ser Arg Asp His Gly Gln Arg Val Thr Cys Arg
            590                 595                 600

Ala His Ser Ala Glu Leu Arg Glu Thr Val Ser Ser Phe Tyr Arg Leu
            605                 610                 615

Asn Val Leu Tyr Arg Pro Glu Phe Leu Gly Glu Gln Val Leu Val Val
            620                 625                 630

Thr Ala Val Glu Gln Gly Glu Ala Leu Leu Pro Val Ser Val Ser Ala
635                 640                 645                 650

Asn Pro Ala Pro Glu Ala Phe Asn Trp Thr Phe Arg Gly Tyr Arg Leu
            655                 660                 665

Ser Pro Ala Gly Gly Pro Arg His Arg Ile Leu Ser Ser Gly Ala Leu
            670                 675                 680

His Leu Trp Asn Val Thr Arg Ala Asp Asp Gly Leu Tyr Gln Leu His
            685                 690                 695

Cys Gln Asn Ser Glu Gly Thr Ala Glu Ala Arg Leu Arg Leu Asp Val
            700                 705                 710

His Tyr Ala Pro Thr Ile Arg Ala Leu Gln Asp Pro Thr Glu Val Asn
715                 720                 725                 730

Val Gly Gly Ser Val Asp Ile Val Cys Thr Val Asp Ala Asn Pro Ile
            735                 740                 745

Leu Pro Gly Met Phe Asn Trp Glu Arg Leu Gly Glu Asp Glu Glu Asp
            750                 755                 760

Gln Ser Leu Asp Asp Met Glu Lys Ile Ser Arg Gly Pro Thr Gly Arg
            765                 770                 775

Leu Arg Ile His His Ala Lys Leu Ala Gln Ala Gly Ala Tyr Gln Cys
            780                 785                 790

Ile Val Asp Asn Gly Val Ala Pro Pro Ala Arg Arg Leu Leu Arg Leu
795                 800                 805                 810

Val Val Arg Phe Ala Pro Gln Val Glu His Pro Thr Pro Leu Thr Lys
            815                 820                 825

Val Ala Ala Ala Gly Asp Ser Thr Ser Ser Ala Thr Leu His Cys Arg
            830                 835                 840

Ala Arg Gly Val Pro Asn Ile Val Phe Thr Trp Thr Lys Asn Gly Val
            845                 850                 855

Pro Leu Asp Leu Gln Asp Pro Arg Tyr Thr Glu His Thr Tyr His Gln
            860                 865                 870

Gly Gly Val His Ser Ser Leu Leu Thr Ile Ala Asn Val Ser Ala Ala
875                 880                 885                 890

Gln Asp Tyr Ala Leu Phe Thr Cys Thr Ala Thr Asn Ala Leu Gly Ser
            895                 900                 905

Asp Gln Thr Asn Ile Gln Leu Val Ser Ile Ser Arg Pro Asp Pro Pro
            910                 915                 920

Ser Gly Leu Lys Val Val Ser Leu Thr Pro His Ser Val Gly Leu Glu
            925                 930                 935

Trp Lys Pro Gly Phe Asp Gly Gly Leu Pro Gln Arg Phe Cys Ile Arg
            940                 945                 950

Tyr Glu Ala Leu Gly Thr Pro Gly Phe His Tyr Val Asp Val Val Pro
955                 960                 965                 970

Pro Gln Ala Thr Thr Phe Thr Leu Thr Gly Leu Gln Pro Ser Thr Arg
            975                 980                 985

Tyr Arg Val Trp Leu Leu Ala Ser Asn Ala Leu Gly Asp Ser Gly Leu
            990                 995                 1000

Ala Asp Lys Gly Thr Gln Leu Pro Ile Thr Thr Pro Gly Leu His Gln
```

```
            1005                1010                1015

Pro Ser Gly Glu Pro Glu Asp Gln Leu Pro Thr Glu Pro Pro Ser Gly
    1020                1025                1030

Pro Ser Gly Leu Pro Leu Leu Pro Val Leu Phe Ala Leu Gly Gly Leu
1035                1040                1045                1050

Leu Leu Leu Ser Asn Ala Ser Cys Val Gly Gly Val Leu Trp Gln Arg
                1055                1060                1065

Arg Leu Arg Arg Leu Ala Glu Gly Ile Ser Glu Lys Thr Glu Ala Gly
            1070                1075                1080

Ser Glu Glu Asp Arg Val Arg Asn Glu Tyr Glu Glu Ser Gln Trp Thr
        1085                1090                1095

Gly Glu Arg Asp Thr Gln Ser Ser Thr Val Ser Thr Thr Glu Ala Glu
1100                1105                1110

Pro Tyr Tyr Arg Ser Leu Arg Asp Phe Ser Pro Gln Leu Pro Pro Thr
1115                1120                1125                1130

Gln Glu Glu Val Ser Tyr Ser Arg Gly Phe Thr Gly Glu Asp Glu Asp
                1135                1140                1145

Met Ala Phe Pro Gly His Leu Tyr Asp Glu Val Glu Arg Thr Tyr Pro
            1150                1155                1160

Pro Ser Gly Ala Trp Gly Pro Leu Tyr Asp Glu Val Gln Met Gly Pro
            1165                1170                1175

Trp Asp Leu His Trp Pro Glu Asp Thr Tyr Gln Asp Pro Arg Gly Ile
            1180                1185                1190

Tyr Asp Gln Val Ala Gly Asp Leu Asp Thr Leu Glu Pro Asp Ser Leu
1195                1200                1205                1210

Pro Phe Glu Leu Arg Gly His Leu Val
                1215

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer exon 2 5'UTR"

(xi) SEQUENCE DESCRIPTION: SEQ ID NO:3:

GAGAAAGCCA GACAGACGCA G                                             21

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer intron 2"

(xi) SEQUENCE DESCRIPTION: SEQ ID NO:4:

AGCTTCCGCT GGTGGCT                                                  17

(2) INFORMATION FOR SEQ ID NO:5:

(i) SEQUENCE CHARACTERISTICS:
        (A) LENGTH: 17 base pairs
        (B) TYPE: nucleic acid
```

-continued

```
        (C) STRANDEDNESS: single
        (D) TOPOLOGY: linear (ii) MOLECULE TYPE: other nucleic acid
        (A) DESCRIPTION: /desc = "primer intron 23"

(xi) SEQUENCE DESCRIPTION: SEQ ID NO:5:

CTCGGGGAGA CCCACCC                                                         17

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer intron 26"

(xi) SEQUENCE DESCRIPTION: SEQ ID NO:6:

CCTGATGCTA ACGGCAGGGC                                                      20
```

NEPHRIN GENE AND PROTEIN

BACKGROUND OF THE INVENTION

Congenital nephrotic syndrome of the Finnish type (CNF, NPHS1, MIM 256300) is an autosomal recessive disorder, and a distinct entity among congenital nephrotic syndromes. It is characterized by massive proteinuria at the fetal stage and nephrosis at birth. Importantly, NPHS1 appears to solely affect the kidney and, therefore, it provides a unique model for studies on the glomerular filtration barrier.

The primary barrier for ultrafiltration of plasma in renal glomeruli comprises three layers; a fenestrated endothelium, a 300–350 nm thick glomerular basement membrane (GBM), and slit pores, i.e. diaphragms located between the foot processes of the epithelial cells. This barrier is a highly sophisticated size-selective molecular sieve whose molecular mechanisms of function are still largely unclarified. It is anticipated that the GBM, a tightly cross-linked meshwork of type IV collagen, laminin, nidogen and proteoglycans, contains pores that restrict the penetration of large proteins and cells, and, additionally, it has been hypothesized that anionic heparan sulfate proteoglycan components contribute to an electric barrier for macromolecules (Kasinath and Kanwar, 1993). The glomerular filter is affected in a large number of acquired and inherited diseases resulting in extensive leakage of plasma albumin and larger proteins leading to nephrotic syndrome and end stage renal disease. Understanding of the molecular mechanisms of the glomerular filtration process and its pathology is of fundamental importance for clinical medicine, which, in turn, may facilitate novel developments for diagnosis and treatment of complications in primary and secondary diseases of the kidney. Genetic diseases with defects in the filtration barrier as major symptoms can serve as models for providing such knowledge.

Congenital nephrotic syndromes (NPHS) form a heterogenous group of diseases characterized by massive proteinuria at or shortly after birth (Rapola et al., 1992). Nephrotic syndrome can be primary, acquired, or a part of other syndromes. Congenital nephrotic syndrome of the Finnish type (CNF, NPHS1) is a distinct entity among NPHS. It is an autosomal recessive disorder with an incidence of 1:10,000 births in Finland, but considerably less in other countries (Norio, 1966; Huttunen, 1976). The disease manifests itself already at the fetal stage with heavy proteinuria in utero, demonstrating early lesions of the glomerular filtration barrier. The pathogenesis of NPHS1 has remained obscure. There are no pathognomonic pathologic features, the most typical histological finding of NPHS1 kidneys being dilation of the proximal tubuli (Huttunen et aL 1980). The kidneys are also large and have been found to contain a higher amount of nephrons than age-matched controls (Tryggvason and Kouvalainen, 1975). Electron microscopy reveals no abnormal features of the GBM itself, although there is a loss of foot processes of the glomerular epithelial cells, a finding characteristic for nephrotic syndromes of any cause. Analyses of GBM proteins, such as type IV collagen, laminin, and heparan sulfate proteoglycan have not revealed abnormal findings in NPHS1 (e.g. see Ljungberg et al. 1993, Kestilä et al. 1994a). NPHS1 is a progressive disease, usually leading to death during the first two years of life, the only life-saving treatment being kidney transplantation (Hohnberg et al. 1995). Importantly, most transplanted patients have, thus far, not developed extrarenal complications, suggesting that the mutated gene product is highly specific for kidney development and/or glomerular filtration function. However, about 20% of the patients have developed post-transplantation nephrosis the cause of which is unknown (Laine et al., 1993; Holmberg et al., 1995).

Due to its high specificity for the glomerular filtration process, NPHS1 provides a unique model disease for studies on this important kidney function. Since there was no strong candidate gene for the disease, we have used the positional cloning approach in our attempts to identify the CNF gene, and have localised the gene to a 150 kb region on chromosome 19q13.1 (Kestilä et al., 1994b; Männikkö et al., 1995). We have identified a novel gene in the critical region and shown it to be mutated in NPHS1. The gene product is a novel transmembrane protein, which in the human embryo shows a high expression level in renal glomeruli.

SUMMARY OF THE INVENTION

The present invention provides for the novel protein Nephrin and the gene encoding for this protein. The present invention encompasses a novel DNA nucleic acid sequence which is the nucleic acid sequence of SEQ ID NO:1 which encodes for the nephrin protein. The present invention also encompasses the protein encoded for by the coding regions of the nucleic acid sequence of SEQ ID NO:1 which has the amino acid sequence of SEQ ID NO:2. In particular, the present invention also encompasses the mature nephrin protein in which the signal peptide has been cleaved off.

The present invention encompasses method, reagents and kits for screening individuals for the presence of mutated Nephrin gene for diagnosis, pre-natal screening, or postnatal screening for susceptibility to glomerular nephrosis or basement membrane disease. In particular, the present invention provides for screening for congenital nephrotic syndromes of the Finnish type (NPHS1).

The present invention provides for methods, reagents and kits for the therapeutic treatment of basement membrane disease associated with defective endogenous Nephrin gene product. Thus the present invention provides for therapeutic treatment using Nephrin protein, and in particular using protein produced by recombinant DNA methods. In addition, the present invention provides for gene therapy using therapeutic nucleic acid constructs containing the Nephrin gene, or substantially similar DNA sequence thereto.

BRIEF DESCRIPTION OF THE DRAWINGS

The invention will be better understood in view of the attached drawings wherein:

FIG. 1A, is a physical map of the 920 kb region between markers D19S208 and D19S224. FIG. 1B, is a diagram of overlapping cosmid clones spanning the 150 kb critical region containing the NPHS1 gene. Location of polymorphic markers are indicated by arrows. FIG. 1C, is a diagram showing the location of five genes, NPHS1, APLP1, A, B, C, characterised and searched for mutations in this study. FIG. 1D, is a drawing showing a schematic structure of the NPHS1 gene;

FIG. 2 shows a northern blot analysis of nephrin expression (the NPHS1 gene product) with mRNA from human embryonic and adult tissues. The northern filters containing 2 ug of human poly(A) RNA from four fetal and eight adult tissues (Clontech) were hybridized with a 1,371 bp nephrin cDNA probe (exons 1–10) made by RT-PCR from fetal kidney poly(A) RNA.

FIG. 4 is a diagram of the Nucleotide-derived amino acid sequence of nephrin (the NPHS1 gene product) and predicted domain structure. FIG. 4A, is the predicted N-terminal signal sequence is 22 residues, the cleavage site being marked with an arrow. A putative transmembrane domain (spanning residues 1,059–1086) is shown in bold and underlined. The putative extracellular part of the protein contains eight Ig-like modules (boxed), and one fibronectin type III-like module adjacent to the transmembrane domain (boxed with a bold line, residues 941–1025). Cysteine residues are indicated by black dots and the ten putative N-glycosylation sites in the extracellular part of the protein are underlined. FIG. 5 shows the results of expression of nephrin mRNA in human embryonic kidney by in situ hybridization.

DETAILED DESCRIPTION OF THE INVENTION

Figure 1:
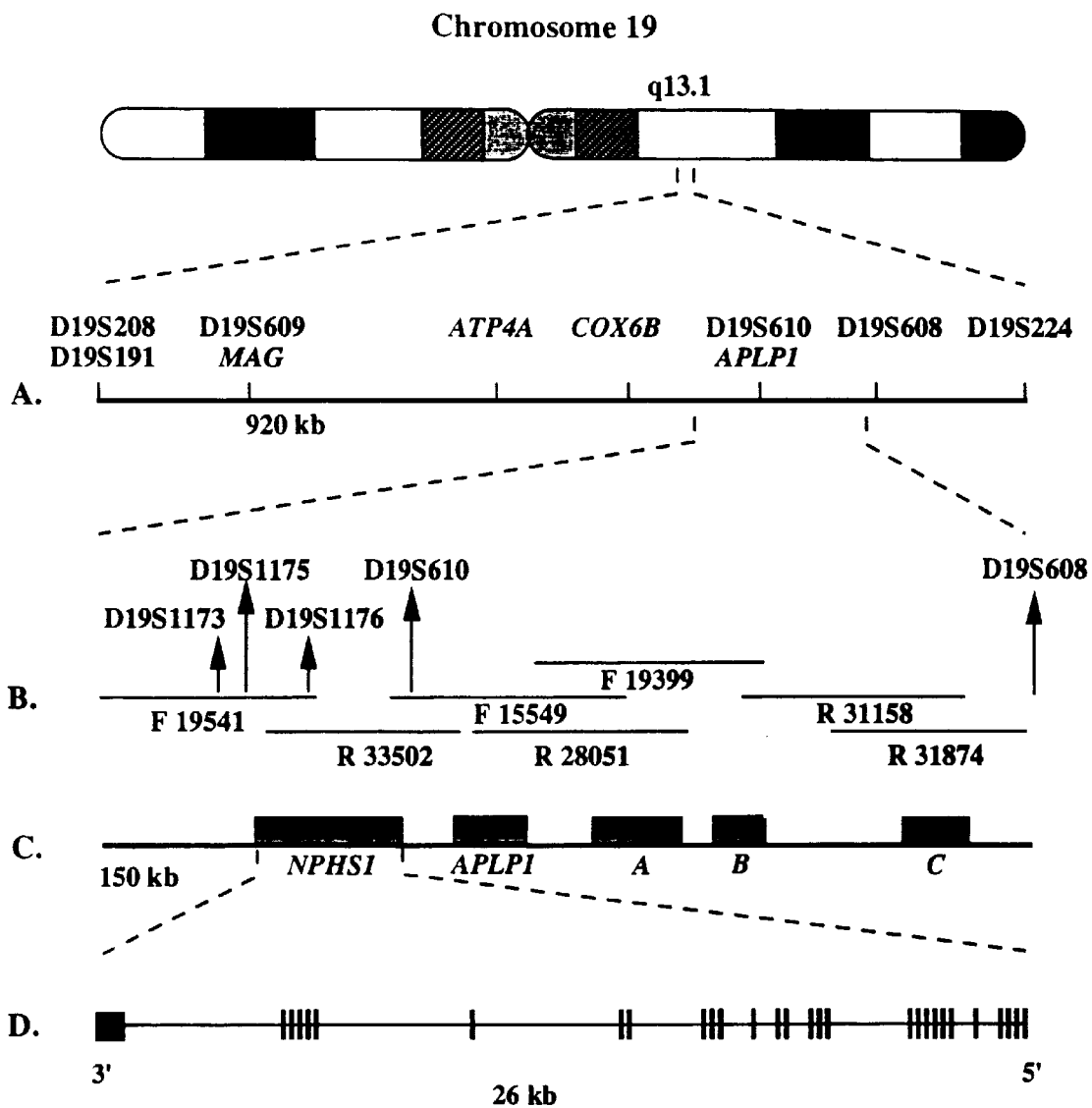
FIG. 1 is a drawing showing a physical map of the NPHS1 locus at 19q13.1 and genomic organisation of the NPHS1 gene.

Congenital nephrotic syndrome of the Finnish type (CNF, NPHS1, MIM 256300) is an autosomal recessive disorder, and a distinct entity among congenital nephrotic syndromes. It is characterized by massive proteinuria at the fetal stage and nephrosis at birth. Importantly, NPHS1 appears to solely affect the kidney and, therefore, it provides a unique model for studies on the glomerular filtration barrier. The NPHS1 gene has been localized to 19q13.1, and in the present study linkage disequilibrium was used to narrow the critical region to 150 kilobases which were sequenced. At least 10 novel genes, and one encoding amyloid precursor like protein were identified in this region. Five of the genes, all of which showed some expression in kidney, were analyzed by sequencing all their 63 exons in NPHS1 patients. Two mutations, a 2-bp deletion in exon 2 and a single base change in exon 26, both leading to premature stop codons were found in a novel 29-exon gene. The mutations were found either as homozygous or compound heterozygous in 44 out of 49 patients, 4 patients having the 2 bp deletion in one allele, the other potential mutation still being unknown. None among controls was found homozygous or compound heterozygous for the mutations. The gene product, termed nephrin, is a 1,241-residue putative transmembrane protein of the immunoglobulin family of cell adhesion molecules which by northern and in situ hybridization was shown to be kidney glomerulus-specific. The results demonstrate a crucial role for nephrin in the development or function of the kidney filtration barrier.

The invention will be more clearly understood by examination of the following examples, which are meant by way of illustration and not limitation.

EXAMPLE 1

Methods and procedures
Sequencing of cosmid clones
Isolation of cosmid clones spanning the region between D19S208 and D19S608 has been reported previously (Olsen et al., 1996). DNA of cosmid clones F19541, R33502, F15549, R28051, F19399, R31158 and R31874 was mechanically sheared by nebulization and fragments of 1000–2000 bp were isolated and subcloned into M13 phage, prior to random sequencing using ABI 377 automated DNA sequencers.
Analysis of seguence
In order to develop new microsatellite markers, repeat regions were searched from the sequence, and three of them (D19S1173, D19S1175, D19S1176) were found to be polymorphic. Homology comparisons were performed using BLASTX and BLASTN programs (Altschul et al., 1990). Prior to BLASTN analyses, the nucleotide sequence was filtered using CENSOR (Jurka et al., 1996) to mask out repeat regions like Alu sequences. Exon prediction was made using GRAIL II (Uberbacher and Mural, 1991), GENSCAN (Burge and Karlin, 1997), FGENEH and HEXON (Solovyeh et al., 1994) programs, and prediction of the protein structure was made using BLASTP (Altschul et al., 1990) and EXPASY molecular biology server (Appel et al., 1994). The mutation search was performed by comparing patient sequences to the normal genomic sequence using the FASTA program of the GCG package (Genetics Computer Group, 1996).
Isolation of cDNAs
cDNAs were generated by PCR from poly(A) RNA from different tissues using primers based on the exon sequences. The PCR fragments were sequenced and used for screening of cDNA libraries. Marathon ready cDNA kits (Clontech Laboratories) were also used to characterize the 5' and 3' extremities of the cDNAs. Comparison of the cDNA and genomic sequences were made to establish the sizes of introns, as were intron sequences at acceptor and donor splice sites.
Southern and Northern blots and in situ hybridization analyses
For Southern analyses samples containing 10 μg of genomic DNA were digested with different restriction enzmes and electrophreses on 1% agarose gels, transferred to nylon membranes and hybridized with the cDNA probe. In multiple-tissue northern analysis poly(A) RNAs from 8 adult and 4 fetal tissues were studied (Clontech). Hybridization was done in ExpressHyb buffer at 65° C. using a cDNA clone containing exons 1–10.

For in situ hybridization a fragment from the NPHS1 cDNA clone (corresponding to exon 10) was labeled with digoxigenin (Boehringer Mannheim), cut to about 150 base pair fragments by alkaline hydrolysis, and then used as a probe. Tissue sections of 7 μm from a 23-week human embryonic kidney were treated with 0.2M HCl, 0.1M triethanolamine buffer, pH 8.0, containing 0.25% (v/v) acetic anhydride and 100 μg/ml proteinase K. The sections were hybridized with the probe at 62° C. for 16 h. After rinsing in 50% formamide and standard sodium citrate, the probe was immunologically detected with an antibody to digoxigenin conjugated to alkaline phosphate enzyme (Boehringer Mannheirn). The color was developed with NBT and BCIP.

Mutation analysis

In this study we analyzed 49 Finnish NPHS1 patients, their parents and a total of 54 healthy siblings. The diagnosis of NPHSl is based on severe proteinuria, a large placenta (>25% of birth weight), nephrotic syndrome during the first weeks of life, and exclusion of other types of congenital nephrotic syndrome (Koskimies 1990). Additionally, samples from 83 control individuals were analysed.

The NPHS1 gene was analysed by PCR-amplifying and sequencing all exon regions from genomic DNA. The sequences of the primers for exon 2 were 5'GAGAAAGC-CAGACAGACGCAG3' (5' UTR) and 5'AGCTTCCGCTG-GTGGCT3' (intron 2), and the sequences of the primers for exon 26 were 5'CTCGGGGAGACCCACCC3' (intron 23) and 5'CCTGATGCTAACGGCAGGGC3' (intron 26). PCR reactions were performed in a total volume of 25 ul, containing 20 ng of template DNA, 1×AmpliTaq buffer (Perkin-Elmer), 0.2 mM of each nucleotide, 50 ng of primers and 0.5 U AmpliTaq Gold DNA polymerase. The reactions were carried out for 30 cycles with denaturation at 95° C. for 1 min, annealing at 60° C. for 1 min, and extension at 72° C. for 1 min. In the first cycle denaturation was carried out for 12 min, and extension in the last cycle was for 8 min. PCR products were separated by 1.5% agarose gel, sliced off and purified by the QiaexII system (Qiagen). The purified PCR product was sequenced using specific primers employing dRhodamine dye-terminator chemistry and an ABI377 automated sequencer (Perkin-Elmer).

When screening for the NPHS1 Fin-major mutation from parents, siblings and controls, a 100 bp PCR product containing the exon 2 deletion site was amplified using a radioactively end-labeled primer, and electrophoresed on 6% polyacrylamide gels. The second NPHS1 Fin-minor mutation could be screened for using a novel restriction site for DdeI. The 140 bp amplified PCR product was digested with DdeI and the products (140 bp or 90 bp+50 bp) were separated on an agarose gel (1% SeaKem agarose—3% NuSieve agarose).

In general, methods and procedures for performing molecular biological and biochemical techniques are known in the art and can be found in available texts and references, such as for example Sambrook et al., (1989) *Molecular Cloning: a laboratory manual,* 2nd edition (Cold Spring Harbor Laboratory Press, Cold Spring Harbor, N.Y.); *Short Protocols in Molecular Biology* 2nd edition (edited by Ausubel et al., John Wiley & Sons, New York, 1992); Davis et al., (1986) *Basic Methods in Molecular Biology* (Elsevier, N.Y.); *Gene Expression Technology* (edited by David Goeddel, Academic Press, San Diego, Calif., 1991).

EXAMPLE 2

Characterization of genes at the CNF locus

Following localisation of the NPHS1 gene to 19q13.1, overlapping cosmid clones from the interval of interest between markers D19S208 and D19S224 were isolated (Männikkö et al. 1995; Olsen et al., 1996). Based on the significant linkage disequilibrium observed with D19S608 and D19S610, as well as the new microsatellite markers, D19S1173, D19S1175, and D19S1176, identified in this study, the NPHS1 gene was fine-mapped between D19S1175 and D19S608, in close vicinity of D19S1176 and D19S610 (FIG. 1). Southern hybridization analyses of NPHS1 patient DNA with genomic clones did not reveal variations, suggesting that the NPHS1 mutations do not represent major genomic rearrangements. The 150 kb critical region was sequenced in its entirety, and the sequence was searched for potential candidate genes using exon prediction programs and data base similarity searches. Based on those analyses, the critical region was estimated to include over 100 potential exons. Similarity searches revealed one previously known gene, i.e. APLP1 encoding an amyloid precursor-like protein (Lenkkeri et al., in press) and eight distinct expressed sequence tags (ESTs). Together, the analyses indicated the presence of at least ten novel genes in the critical region.

FIG. 1 illustrates a physical map of the NPHS1 locus at 19q13.1 and genomic organisation of the NPHS1 gene. FIG. 1A, Physical map of the 920 kb region between D19S208 and D19S224. FIG. 1B, Overlapping cosmid clones spanning the 150 kb critical region containing the NPHS1 gene. Location of polymorphic markers are indicated by arrows. FIG. 1C, Location of five genes, NPHS1, APLP1, A, B, C, characterised and searched for mutations in this study. FIG. 1D, Schematic structure of the NPHS1 gene.

Using Grail and Genscan exon prediction programs and sequences from cDNAs, the exon/intron structures of five of the genes, NPHS1 (FIG. 1), APLP1, A, B, and C (not shown) were determined. Although steady state transcript levels varied, northern analyses revealed expression of all the genes in kidney, and with the exception of NPHS1, also in other tissues. Therefore, none of them could be excluded as the NPHS1 gene and all were subjected to mutation analysis.

EXAMPLE 3

Identification of the NPHS1 gene

Haplotype analyses of NPHS1 chromosomes have revealed two major classes in Finnish patients (Männikkö al., 1995; this study). The first one containing haplotypes 1-1-1-6-g-2-8-9 and 1-1-1-6-g-6-4-2 (markers D19S1173, D19S1175, D19S1176, D19S610, RFLP of gene B, D19S608, D19S224, D19S220, respectively) is the most common one found in 78% of Finnish NPHS1 chromosomes. The second haplotype class, 3-5-3-6-a-8-10-x, is found in 13% of cases. The remaining 9% of observed haplotypes show totally different allele combinations, and have been thought to represent other mutations. Two major haplotype classes could represent the same mutation, because they both share allele 6 of D19S610. However, the present results demonstrated that they represent two different mutations.

Since Southern hybridization analyses did not reveal any major gene rearrangements, mutations were searched by direct sequencing of PCR-amplified exon regions of, if necessary, all the genes of this region.

The 17 exon APLP1 gene located distal to D19S610 did not show variations between patients and controls, and was excluded as the NPHS1 gene (Lenkkeri et al., in press). Also, the novel genes A, B and C, containing 9, 5 and 3 exons, respectively, did not have sequence variants segregating with NPHS1, and could similarly be excluded as the NPHS1 genes (data not shown). A fourth novel gene (NPHS1) located proximal to D19S610 encoding a transcript of about 4.3 kb was shown to be strongly expressed in human embryonic and adult kidneys, no clear signals above background being observed in other tissues (FIG. 2).

Figures 2A, 2B:
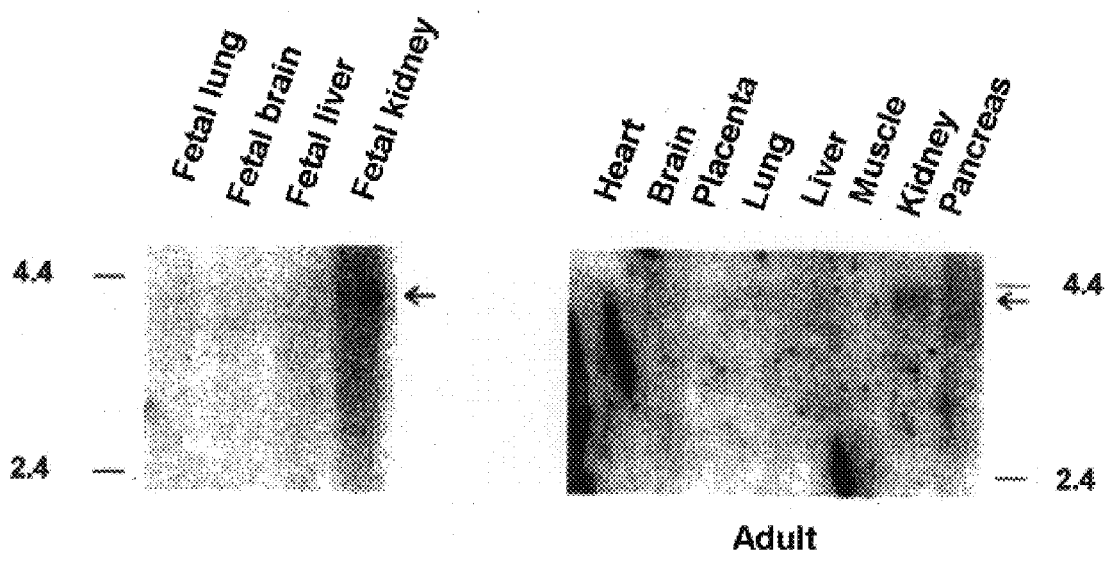
FIG. 2A, shows distinct expression can be seen only with fetal kidney RNA (arrow).
FIG. 2B, shows results using RNA from adult tissues, intense signal is only observed in a 4.3 kb band with kidney RNA (arrow), the other tissues exhibiting only insignificant if any positive signals. The tissues studied are marked above the filter and molecular size markers (kb) are shown to the sides of the filters.

FIG. 2 illustrates the results of Northern analysis of nephrin expression with mRNA from human embryonic and adult tissues. The northern filters containing 2 ug of human poly(A) RNA from four fetal and eight adult tissues (Clontech) were hybridized with a 1,371 bp nephrin cDNA probe (exons 1–10) made by RT-PCR from fetal kidney poly(A) RNA. In FIG. 2A, Distinct expression can be seen only with fetal kidney RNA (arrow). In FIG. 2B, Using RNA from adult tissues, intense signal is only observed in a 4.3 kb band with kidney RNA (arrow), the other tissues exhibiting only insignificant if any positive signals. The tissues studied are marked above the filter and molecular size markers (kb) are shown to the sides of the filters.

Therefore, this gene was a strong candidate for NPHS1. Full-length cDNA for the transcript was constructed using fetal kidney poly(A) mRNA (Clontech) and PCR primers made based on the predicted exon structure. The gene was found to have a size of 26 kb and to contain 29 exons (FIG. 1).

Figure 3:
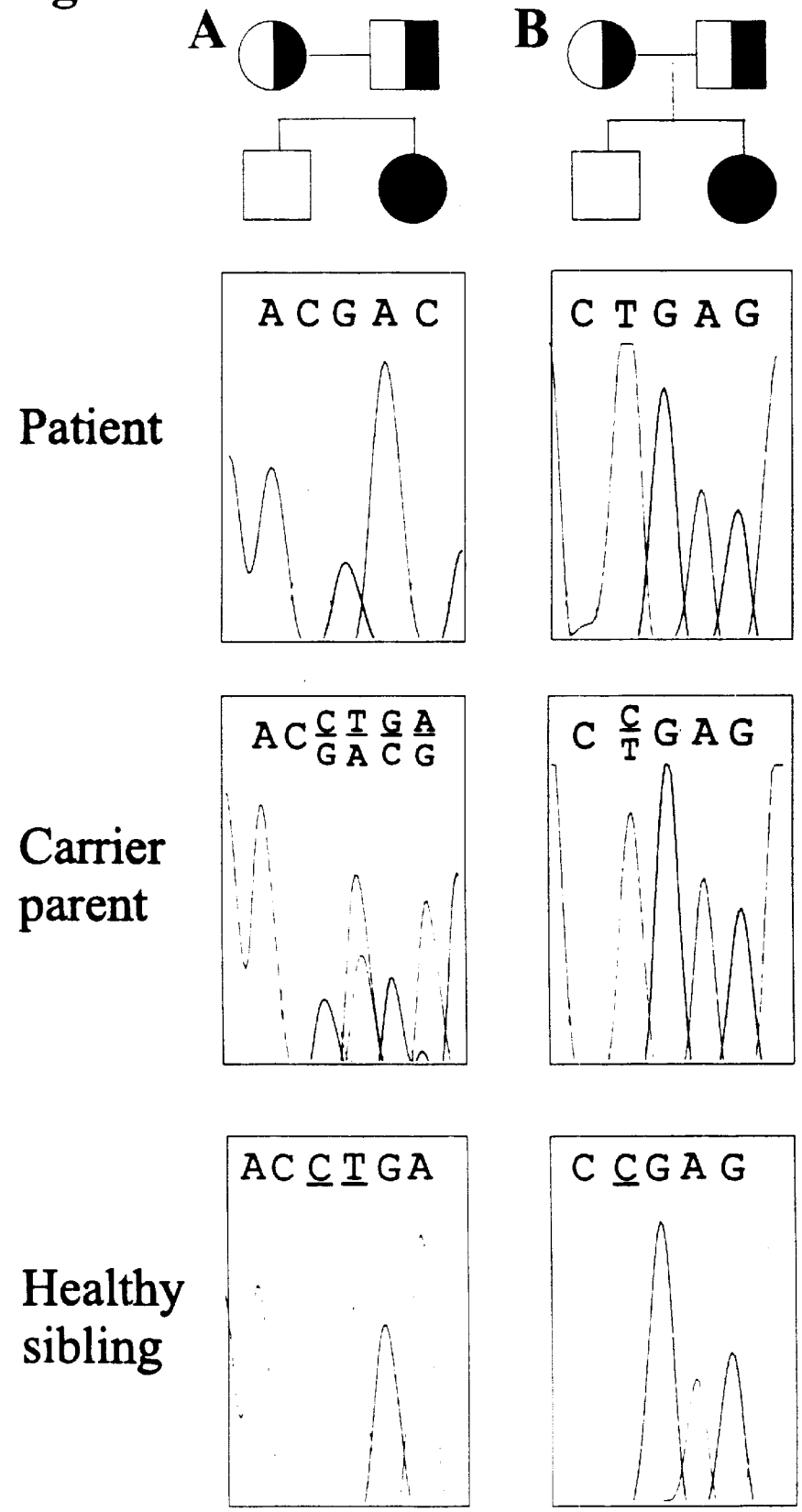
FIG. 3 is a diagram of Mutation analysis of the NPHS1 gene. Left: (A) Pedigree of an NPHS1 family with an affected child having a 2-bp deletion in exon 2. Sequences of the deletion point shown from patient (homozygous), parent (heterozygous) and a healthy sibling. Right: (B) Pedigree of an NPHS1 family with an affected child having a nonsense mutation in exon 26. Sequences of the mutated region are shown from patient (homozygous), parent (heterozygous) and a healthy sibling.

Exon sequencing analyses revealed the presence of two major mutations in over 90% of NPHS1 chromosomes (FIG. 3). FIG. 3 illustrates mutation analysis of the NPHS1 gene. Left: (A) Pedigree of a NPHS1 family with an affected child having a 2-bp deletion in exon 2. Sequences of the deletion point shown from patient (homozygous), parent (heterozygous) and a healthy sibling. Right: (B) Pedigree of a NPHS1 family with an affected child having a nonsense mutation in exon 26. Sequences of the mutated region are shown from patient (homozygous), parent (heterozygous) and a healthy sibling.

The first mutation, a 2-bp deletion in exon 2 causes a frameshift resulting in the generation of a stop codon within the same exon. This mutation was found in all NPHS1 chromosomes with the haplotype 1-1-1-6-g-2-8-9 and 1-1-1-6-g-6-4-2 (total of 76 chromosomes). One out of 83 control individuals was heterozygous for the Fin-major mutation. The second sequence variant found in the NPHS1 gene was a nonsense mutation CGA->TGA in exon 26, present in patients with haplotype 3-5-3-6-a-8-10-x (13 chromosomes), and three patients with different haplotypes. None of the parents, healthy siblings, or controls (total of 230 individuals) were homozygous or compound heterozygous for the two mutations identified here. Since the gene cloned in this study is the one involved in a hereditary nephrotic syndrome, we refer to it as NPHS1 gene.

Out of 49 NPHS1 patients studied, 32 were homozygous for the 2-bp deletion in exon 2 (Fin-major), four were homozygous for the nonsense mutation in exon 26 (Fin-minor), and eight were compound heterozygotes. Four patients had the Fin-major mutation in one allele, the other potential mutation still being unknown. One patient had neither one of the two mutations.

EXAMPLE 4

Characterization of the NPHS1 gene product

The cDNA-predicted amino acid sequence of the NPHS1 protein (nephrin) is 1,241 residues (FIG. 4), with a calculated molecular mass of 134,742 without posttranslational modifications.

Figure 4B:
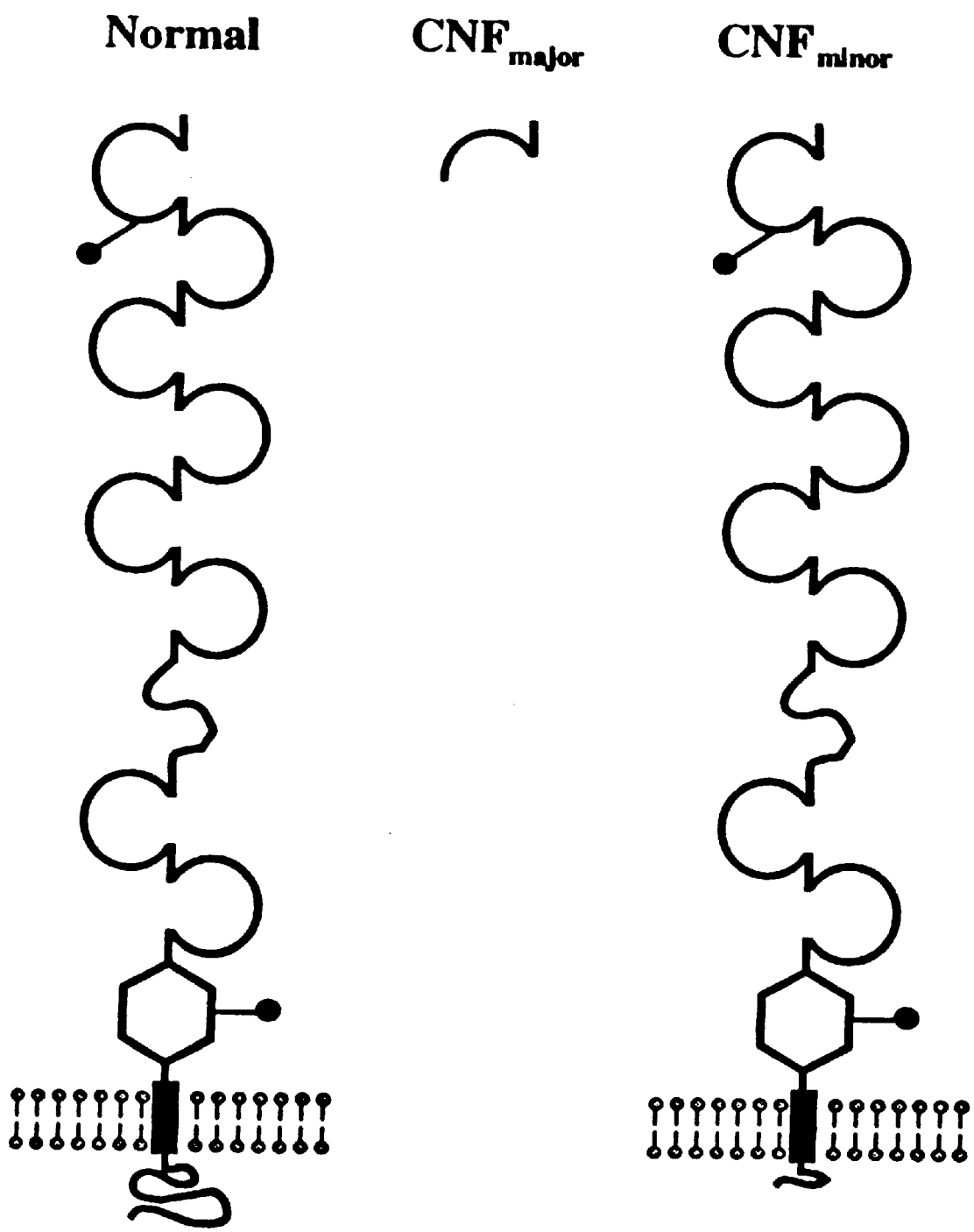
FIG. 4B shows the predicted domain structure of normal nephrin and the predicted effects of the two mutations (Fin-major and Fin-minor) identified in this study. The Ig-like modules are depicted by partial circles and the fibronectin type III like-motif by a hexagon. The transmembrane domain is shown as a black rectangle located in a membrane lipid bilayer. The locations of two free cysteine residues are indicated by lines with a black dot at the end. The Fin-major mutation would result in the production of part of the signal peptide and a short nonsense sequence. The Fin-minor mutation would result in a nephrin molecule lacking a part of the cytosolic domain.

FIG. 4 shows Nucleotide-derived amino acid sequence of nephrin and predicted domain structure (the NPHS1 gene product). FIG. 4A illustrates the predicted N-terminal signal sequence is 22 residues, the cleavage site being marked with an arrow. A putative transmembrane domain (residues 1,059–1086) is shown in bold and underlined. The putative extracellular part of the protein contains eight Ig-like modules (boxed), and one fibronectin type III-like module adjacent to the transmembrane domain (boxed with a bold line). Cysteine residues are indicated by black dots and the ten putative N-glycosylation sites in the extracellular part of the protein are underlined. FIG. 4B illustrates predicted domain structure of normal nephrin (the NPHS1 gene product) and the predicted effects of the two mutations (Fin-major and Fin-minor) identified in this study. The Ig-like modules are depicted by partial circles and the fibronectin type III like-motif by a hexagon. The transmembrane domain is shown as a black rectangle located in a membrane lipid bilayer. The locations of three free cysteine residues are indicated by lines with a black dot at the end. The major NPHS1 mutation would result in the production of a secreted protein containing only a part of the first Ig-like module. The Fin-minor mutation would result in a nephrin molecule lacking a part of the cytosolic domain.

Several similarity comparison and protein structure prediction programs predicted that the NPHS1 protein would be a transmembrane protein of the immunoglobulin superfamily. There is a tentative 22-residue-long N-terminal signal peptide, an extracellular domain containing eight immunoglobulin-like domains, one fibronectin type III domain-like module, followed by a single putative transmembrane domain-like sequence, and a cytosolic C-terminal end. In spite of the presence of known structural modules (FIG. 4), the sequence identity with corresponding domains of proteins in the data base was relatively low. The tentative extracellular portion of the protein contains ten NXS or NXT consensus triplets for N-glycosylation. Furthermore, there are seven SG doublets, that are potential attachment sites for heparan sulfate.

Northern hybridization analysis carried out with poly(A) mRNA from four human embryonic and eight adult tissues revealed a high steady state level of the NPHS1 gene transcript in the kidney, but not notably in other tissues. (FIG. 2). In situ hybridization carried out on a kidney sample from a 23-week-old human embryo revealed intense expression signals in the glomeruli (FIG. 5 A). At higher magnification (FIG. 5 B), the signals could be seen in the periphery of mature and developing glomeruli, while the central mesangial regions are negative. It is apparent that the positive cells are epithelial podocytes. No specific signals were obtained with the antisense control probe.

Figure 5A:
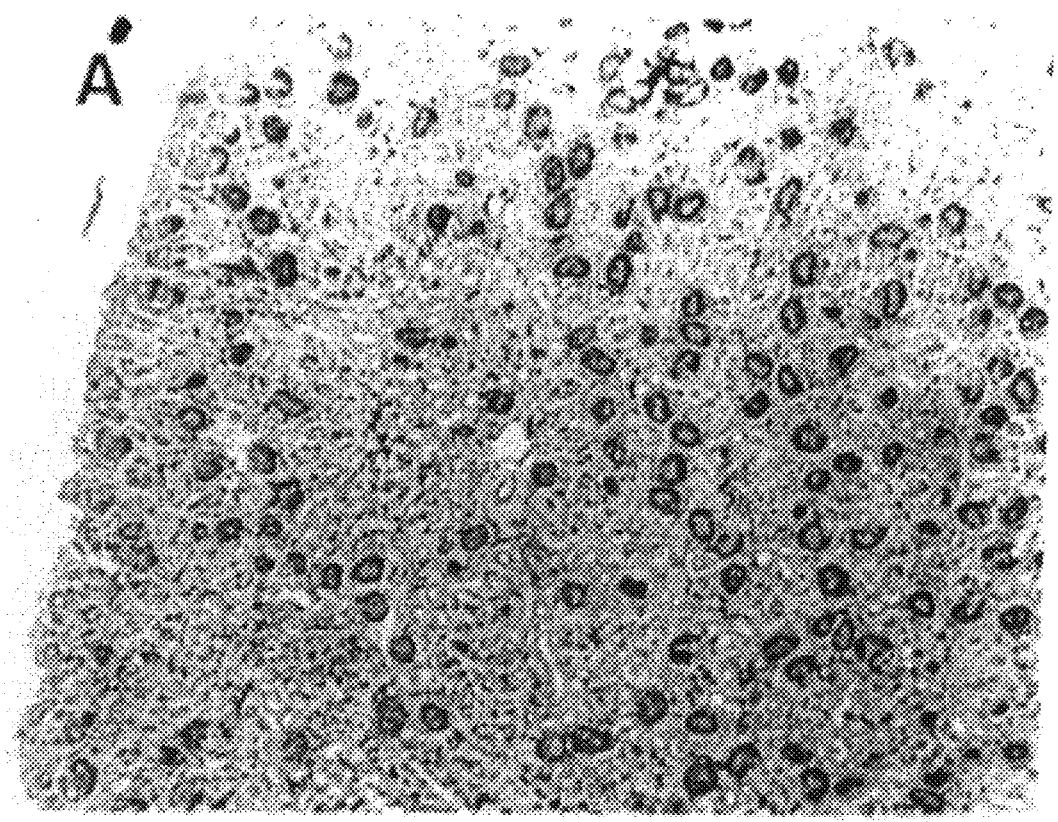
FIG. 5A, shows intense expression in glomeruli throughout the renal cortex, little if any specific expression being observed in other structures. (4×objective magnification).
Figure 5B:
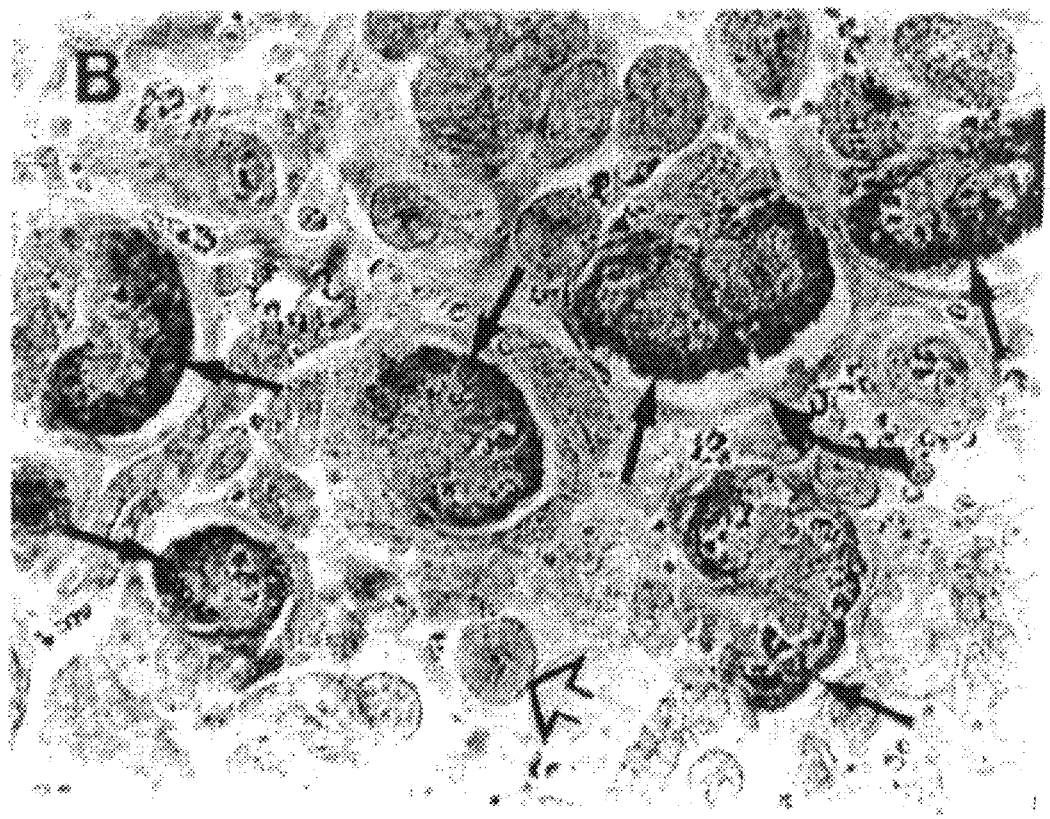
FIG. 5B, is a view at higher magnification which reveals intense expression in the periphery of individual glomeruli (straight arrows), probably mainly in epithelial cells. No expression is observed in the Bowman's capsule (bent arrow), proximal tubuli (open arrows), or endothelial cells of vessel walls. (20×objective magnification).

FIG. 5 illustrates expression of nephrin mRNA in human embryonic kidney by in situ hybridization. FIG. 5A shows intense expression is seen in glomeruli throughout the renal cortex, little if any specific expression being observed in other structures. (4×objective magnification). FIG. 5B, Higher magnification reveals intense expression in the periphery of individual glomeruli (straight arrows), probably mainly in epithelial cells. No expression is observed in the Bowman's capsule (bent arrow), proximal tubuli (open arrows), or endothelial cells of vessel walls. (20×objective magnification).

EXAMPLE 5

The NPHS1 gene and its gene product nephrin

Several lines of evidence obtained in the present study show that we have positionally cloned the gene affected in congenital nephrotic syndrome of the Finnish type. First, the defective gene is located in the critical 150 kb region on chromosome 19q13.1 to which the gene has been localized using linkage disequilibrium analyses (Kestilä et al., 1994b; Männikkö et al., 1995; Kestilä et al. manuscript). Second, the two mutations identified in the study were shown to be present, either as homozygous or compound heterozygous mutations, in 44 out of 49 Finnish patients studied. Four of the remaining patients had the major mutation in one allele, the mutation in the other allele being, as yet, unidentified. One patient who did not have either of the two mutations, has a unique haplotype and, therefore, probably carries a different mutation. Third, individuals homozygous or compound heterozygous for the mutations were not found in 230 control DNAs. Additional, indirect evidence was the strong and practically renal glomeruli-specific expression of the gene, which implies involvement of the gene product in glomerular development or function.

Identification of the NPHS1 gene

The present identification of the NPHS1 gene demonstrates the power of linkage disequilibrium analysis and direct DNA sequencing in the positional cloning of disease genes containing small mutations. Here, linkage disequilibrium mapping (Hästbacka et al., 1994) which when used with DNA from individuals of a homogenous population, such as the isolated Finnish population (de la Chapelle, 1993), was utilized to localize the NPHS1 gene to a 150 kb genomic segment. In order to find genes located in this region, the entire segment was first sequenced, and using a combination of exon prediction programs and homology comparison analyses we could construct remarkably accurate gene structures that were verified from cDNAs. These cDNAs could be isolated either with the use of EST clones or by using the predicted exon sequences to construct cDNAs by PCR from mRNA. In this manner we could quickly identify 11 genes within the 150 kb NPHS1 containing genomic segment. Since none of the genes was an obvious candidate for NPHS1, and no major gene rearrangements, such as deletions, insertions or inversions, were found in patient DNAs, search for small mutations had to be initiated, if necessary, in all the 11 genes. Having determined the exon and cDNA sequences for the genes, methods such as SSCP and DGGE, which are frequently used for identification of small mutations, were potential alternatives. However, our experience from the search for small mutations in Alport syndrome (Barker et al., 1990; Tryggvason, 1996) suggests that these methods can frequently yield false negatives. For example, SSCP analyses in quite large patient populations have revealed only a 35–50% mutation detection rate (Kawai et al., 1996, Knebelmann et al. 1996, Renieri et al., 1996), while our direct sequencing of PCR-amplified exon regions has yielded over 80% detection We therefore decided to use direct sequencing of exon regions to find the NPHS1 mutations. Although we had to sequence numerous exons of several genes, this relatively soon resulted in the identification of two small mutations in one gene. We conclude that sequencing of even a large candidate gene region and direct sequencing of its genes is an attractive and, above all, reliable method to search for small mutations in positional cloning, particularly if only few mutations can be expected to be present.

Genetics of NPHS1

Crucial components in the successful positional cloning of the NPHS1 gene were the small isolated population, good clinical records and equal, high quality health care system which made it possible to reliably collect family samples. A typical situation in population isolates is that close to 100% of cases are caused by the same mutation, and this phenomenon can already be seen in haplotype analysis. Observed changes in the founder haplotype, caused by historical recombinations, can be used to restrict the critical chromosomal region to a short genomic segment. Thus, differences in the major NPHS1 haplotype 1-1-1-6-g-2-8-9 enabled substantial narrowing of the interval, leading to the isolation of the NPHS1 gene. The major NPHS1 mutation causes only 78% of cases, in contrast to many other "Finnish diseases" with 95–98% prevalence of major disease alleles (e.g. Ikonen et al., 1991). However, the two main NPHS1 mutations characterized in this study together represent 94% of Finnish cases.

Congenital nephrotic syndrome of the Finnish type is enriched in the Finnish population, but several cases can be found worldwide. Considerable immigration from Finland to Minnesota has also caused the spread of NPHS1 to the USA (Norio 1966; Mahan et al., 1984). In addition, several CNF cases have been diagnosed in different European countries, and linkage studies have supported association of analyzed families to the same chromosome 19 locus (Fuchshuber et al., 1996).

The identification of the NPHS1 gene and disease causing mutations have immediate clinical significance, as they have enabled the development of exact DNA-based diagnosis for NPHS1 and carrier screening. This is particularly important, as we have recently demonstrated that the screening method widely used in Finland for NPHS1 based on measurements of alpha-fetoprotein levels in amniotic fluid can lead to false positive results and subsequent abortions of healthy NPHS1 carriers (Männikkö et al., 1997).

Nephrin—a glomerulus-specific cell adhesion receptor

Due to the high association of expression and pathology with glomeruli, the proximal part of the nephron, we have named the NPHS1 gene product nephrin. The role of nephrin remains unknown, but it is likely to be an adhesion receptor and a signaling protein, as its domain structure resembles that of a large group of cell adhesion receptors belonging to the immunoglobulin superfamily (Brümmendott and Rathjen, 1994).

The Ig-like domains of nephrin are all of type C2 which is particularly found in proteins participating in cell—cell or cell-matrix interactions. Between the sixth and seventh Ig-like domains there is a spacer of about 130 residues containing an unpaired cysteine, and there is another unpaired cysteine in the fibronectin type III-like domain. Their SH groups could be involved in the formation of cis homo/heterodimers, participate in thioether or thioester bonds with unknown structures, or be buried within the domains, as suggested by Brümmendott and Rathjen (1994).

Data base searches revealed that the cytosolic domain that contains nine tyrosine residues of nephrin has no significant homology with other known proteins. However, sequence motifs surrounding tyrosines suggest that tyrosines 1176, 1192 and 1217 could become phosphorylated during ligand binding of nephrin (see, Songyang et al. 1993). In that case, binding sites for the SH2-domains of Src-family kinases, Abl-kinase, and an adaptor protein Nck might be created (tyrosines 1176 and 1192 are followed by the motif DEV, and tyrosine 1217 by DQV). The crucial role for the intracellular domain of nephrin is emphasized by the fact that the Fin-minor mutation which results in the loss of 132 out of 155 residues results in full blown NPHS1.

The pathogenesis of NPHS1 has been thought to primarily or secondarily involve the highly anionic glycosaminoglycans, as the content of such molecules that are considered important for the glomerular filtration process is reported to be decreased in the GBM in proteinuria (Kasinath and Kanwar, 1993). It cannot be excluded that nephrin is a proteoglycan, as it has several SG consensus sites for heparan sultate side chains, including the triplet SGD which is the major attachment sequence for the three large heparan sulfate side chains in the basement membrane proteoglycan perlecan (Noonan et al., 1991; Kallunki and Tryggvason, 1992; Dolan et al., 1997). However, thus far no Ig-like receptors have been reported to contain glycosaminoglycans.

How does nephrin function and what is its role in glomerular function? A vast majority of similar receptors interact with other membrane proteins in a homo- or heterophilic manner. However, some of the receptors have been shown to interact with extracellular matrix (ECM) proteins. For example, the myelin-associated glycoprotein MAG whose extracellular domain contains five Ig-like domains, interacts with different types of collagens and glycosaminoglycans (Fahrig et al., 1987). Furthermore, the axonal glycoprotein F11 and the deleted in colorectal cancer (DCC) protein have both been shown to bind tenascins and netrins, respectively (Zisch et al., 1992; Pesheva et al., 1993; Keino-Masu, 1996). Since it is possible that nephrin either binds another membrane protein or a protein of the ECM, which in this case would be the GBM, it will be important to localize nephrin by immunoelectron microscopy before embarking on the search for a specific ligand.

Whatever its function, the in situ hybridization analyses strongly suggested that nephrin is produced in glomerular epithelial cells that form the foot processes partially covering the outside of the glomerular capillaries. The ultimate filtration barrier for plasma macromolecules is located in the diaphragm covering the slit pores between the foot processes. In NPHS1 and nephrotic syndromes of other causes, fusion of the foot processes is a general finding, and the structure or function of the slit pores are somehow affected with proteinuria as a result. It is proposed that the plasma membrane protein nephrin is important for maintaining the integrity of the foot processes of glomerular epithelial cells, or is crucial for their anchorage to components of the GBM.

Conclusions

The identification of the NPHS1 gene will immediately find applications for diagnosis of the disease. Studies on the gene product nephrin, a putative cell adhesion and signaling receptor, may also provide a key to new fundamental knowledge on the molecular mechanisms of glomerular filtration, which despite decades of research are still poorly understood. As abnormal function of the filtration barrier is a major complication in many clinically important kidney diseases, such as diabetic nephropathy, nephrotic syndromes and glomerulonephritides, the present work is likely to have a more general impact on clinical nephrology. Immediate questions relate to the developmental expression and location of the protein, which would require the generation of antibodies and nucleotide probes for studies in animal and cell culture systems.

EXAMPLE 6
Genetic Screening for Basement Membrane Disease

With the identification and characterisation of nephrin as a critical component in basement membrane disease associated with glomerular nephropathy, it is now possible to screen individuals, both pre- and post-natal screening, for susceptibility for basement membrane disease by detecting mutated nephrin gene or protein. Such information will be useful to medical practitioners for the future diagnosis of disease conditions in screened individuals, and for planning preventative measures for the possible containment of future disease. Such information will be useful for the diagnosis of currently active disease conditions. The present invention allows for the diagnosis of currently active disease conditions, as being related to basement membrane disease by detecting mutated nephrin gene or protein. The discovery of the nephrin gene provides a means for detecting the presence of the nephrin gene in individuals, and for the determination of the presence of any mutations in said gene. Such means for detection comprises nucleic acids having the entire nephrin gene sequence, or fragments thereof which will specifically hybridize to said nephrin gene, or mRNA transcripts from said nephrin gene under stringent conditions. An additional means for detection of the nephrin gene and mutations therein comprise specific contiguous fragments of said gene, and complementary gene sequence, which can be combined for use as primers for amplifying the targeted gene sequence. Said means for detection of mutations in a nephrin gene also comprise direct hybridization of normal gene with target gene and subsequent detection of successful hybridization. In all cases, the target gene may be amplified or unamplified DNA or RNA isolated from the individual to be tested.

Antibody Screening of Tissues and Samples

By having the NPHS1 gene sequence, it is well within the skill of one in the art to use existing molecular biology and biochemical techniques to construct and use an expression vector which will produce recombinant nephrin protein, or fusion protein, purify this protein, and produce antibodies specifically reactive with nephrin. The expression of proteins in bacterial, yeast, insect and mammalian cells is known in the art. It is known in the art how to construct and use expression vectors in which the expressed gene contains one or more introns. The production of monoclonal antibodies is well known in the art, and the use of polyclonal and monoclonal antibodies for immunohistochemical detection of protein in tissue samples is a routine practice. A wide variety of detectable labels are available for use in immunohistochemical staining and immunoassays for detection of protein in samples such as homogenised tissue, blood, serum, urine or other bodily fluids.

One of ordinary skill in the art will be able to readily use the teachings of the present invention to design suitable assays and detection schemes for practising the screening methods contemplated by the present invention.

Gene Therapy

Given the teaching of the present invention, it will be possible to address deficiencies in Nephrin gene or protein by gene therapy or therapy using recombinant protein. Methods for the administration of protein and gene therapy are known in the art.

GenBank Accession Numbers

The accession numbers for the cosmid clones characterised are: F19541=U95090, R33502=AC002133, R28051=AD000864, F19399=AD000833, R31158=AD000827, R31874=AD000823. The accession for the nephrin cDNA sequence is AF035835.

One of ordinary skill in the art will be able to readily use the teachings of the present invention to design and construct suitable nucleic acid sequences which will be the functional equivalents of those disclosed. One of ordinary skill in the art will know that there exisits many allelic variants of the disclosed nucleic acid sequnences which still encode for a nephrin protein with equivalent function. The teaching of the present invention allows for the discovery of mutations in the nephrin gene and the modified protein therein encoded.

EXAMPLE 7
Screening for Small Molecule Therapeutics

With the identification and characterisation of nephrin as a critical component in kidney pathothogy and proteinuria, and thus implicated in many kidney diseases, it is now possible to screen for small molecule therapeutics using nephrin and the neprhin gene. Screening for such therapeutics can be accomplished by sequential selective screening for activity and molecules which specifically hybridize to nephrin, or which specifically effect the expression of the neprhrin gene. Selective screening can be performed on pools of small molecule compounds generated by standard combinatorial chemistry, on known moleucles, or in combination with computer modeling of the nephrin protein structure and rational drug design. Such methods and techniques are known in the art.

Literature Cited

Altschul, S. F., Gish, W., Miller, W., Myers, E. W., and Lipman, D. J. (1990) Basic local alignment search tool. J. Mol. Biol. 215, 403–10

Appel, R. D., Bairoch, A. and Hochstrasser, D. F. (1994) A new generation of information retrieval tools for biologists: the example of the ExPASy WWW server. Trends Biochem. Sci. 19: 258–260

Barker, D., Hostikka, S. L., Zhou, J., Chow, L. T., Oliphant, A. R., Gerken, S. C., Gregory, M. C., Skolnick, M. H., Atkin, C. L. and Tryggvason, K. (1990) Identification of mutations in the COL4A5 collagen gene in Alport syndrome. Science 248, 1224–1227

Brümmendott, T., and Rathjen, F. G. (1994) Cell adhesion molecules 1: Immunoglobulin superfamily. Protein profile 1, 951–1058

Burge, C. and Karlin, S. (1997) Prediction of complete gene structures in human genomic DNA. J. Mol. Biol. 268, 78–94.

de la Chapelle, A. (1993) Disease gene mapping in isolated human populations: the example of Finland. J. Med. Genet. 30:857–865

Dolan, M., Horchar, T., Rigatti, B., and Hassell, J. R. (1997) Identification of sites in domain I perlecan that regulate heparan sulfate synthesis. J. Biol. Chem. 272, 4316–4322

Fahrig, T., Landa, C., Pesheva, P., Kühn, K., and Schacher, M. (1987) Characterization of binding properties of the myelin-associated glycoprotein to extracellular matrix constituents. EMBO J. 6, 2875–2883

Fuchshuber, A., Niaudet, P., Gribouval, O., Genevieve, J., Gubler, M-C., Broyer, M. and Antignac, C. (1996) Congenital nephrotic syndrome of the Finnish type: linkage to the locus in a non-Finnish population. Pediatr. Nephrol. 10: 135–138

Genetics Computer Group, Program manual for the Wisconsin Package, Version 9, December, 1996, 575 Science Drive, Madison, Wis., USA 53711

Hästbacka, J., de la Chapelle, A., Mahtani, M. M., Clines, G., Reeve-Daly, M. P., Daly, M., Hamilton, B. A., Kusumi, K., Trivedi, B., Weaver, A., Coloma, A., Lovett, M., Buckler, A., Kaitila, I., and Lander, E. S. (1994) The diastrophic dysplasia gene encodes a novel sulfate transporter: positional cloning by fine-stucture linkage disequilibrium mapping. Cell 78, 1073–1087

Holmberg, C., Antikainen, M., Rönnholm, K., Ala-Houhala, M. and Jalanko, H. (1995) Management of congenital nephrotic syndrome of the Finnish type. Pediatr. Nephrol. 9: 87–93

Huttunen, N. P., Rapola, J., Vilska, J. and Hallman, N. (1980) Renal pathology in congenital nephrotic syndrome of the Finnish type: a quantitative light microscopic study on 50 patients. Int. J. Pediatr. Nephr. 1: 10–16

Ikonen, E., Baumann, M., Grön, K., Syvänen, A-C., Enomaa, N., Halila, R., Aula, P. and Peltonen, L. (1991) Aspartylglucosaminuria: cDNA encoding human aspartylglucosaminidase and the missense mutation causing the disease. EMBO J. 10: 51–58

Jurka, J., Klonowski, P., Dagman, V., Pelton, P. (1996) CENSOR—a program for identification and elimination of repetitive elements from DNA sequences. Computers and Chemistry Vol. 20 (No. 1); 119–122

Kallunki, P., and Tryggvason, K. (1992) Human basement membrane heparan sulfate proteoglycan core protein: a 467 kD protein containing multiple domains resembling elements of the low density lipoprotein receptor, laminin, neural cell adhesion molecules, and epidermal growth factor. J. Cell Biol. 116, 559–571

Kasinath, B. S. and Kanwar, Y. S. (1993) Glomerular basement membrane: biology and physiology. In: Molecular and cellular aspects of basement membranes (D. Rorhbach and R. Timpl, eds), Academic Press, pp. 89–106

Kawai, S., Nomura, S., Harano, T., Fukushima, T., & Osawa, G.(1996) The COL4A5 gene in Japanese Alport syndrome patients: spectrum of mutations of all exons. Kidney Int. 49, 814–822

Keino-Masu, K., Masu, M. Hinck, L., Leonardo, E. D., Chan, S. S. Y., Culotti, J. G., and Tessier-Lavigne, M. (1996) Cell 87, 175–185

Kestilä, M., Männikkö, M., Holmberg, C., Korpela, K., Savolainen, E. R., Peltonen, L. and Tryggvason, K. (1994a) Exclusion of eight genes as mutated loci in congenital nephrotic syndrome of the Finnish type. Kidney Int. 45, 986–990

Kestilä, M., Männikkö, M., Holmberg, C., Gyapay, G., Weissenbcah, J., Savolainen, E. R., Peltonen, L. and Tryggvason, K. (1994b) Congenital nephrotic syndrome of the Finnish type maps to the long arm of chromosome 19. Am. J. Hum. Genet. 54, 757–764

Knebelmann, B., Breillat, C., Forestier, L., Arrondel, C., Jacassier, D., et al. (1996) Spectrum of mutations in the COL4A5 collagen gene in X-linked Alport syndrome. Am. J., Hum. Genet. 59, 1221–1232

Koskimies, O. (1990) Genetics of congenital and early infantile nephrotic syndromes. In: Spitzer, A., Avner, E. D. (eds) Inheritance of kidney and uritary tract diseases. Kluwer, Boston, Dordrecht and London, p. 131–138

Laine, J., Jalanko, H., Holthofer, H., Krogerus, L., Rapola, J., von Willebrand, E., Lautenschlager, I., Salmela, K. and Holmberg, C. (1993) Post-transplantation nephrosis in congenital nephrotic syndrome of the Finnish type. Kidney Int. 44: 867–874

Lenkkeri, U., Kestilä, M., Lamerdin, J., McCready, P., Adamson, A., Olsen, A. and Tryggvason, K. Structure of the human amyloid precursor like protein gene APLP1 at 19q13.1. Human Genetics, in press Ljungberg, P., Jalanko, H., Holmberg, C. and Holthöfer, H. (1993) Congenital nephrosis of the Finnish type (CNF): matrix components of the glomerular basement membranes and of cultured mesangial cells. Histochem. J. 25: 606–612

Mahan, J. D., Mauer, S. M. Sibley, R. K. and Vernier, R. L. (1984) Congenital nephrotic syndrome: Evolution of medical management and results of renal transplantation. J. Pediatr. 105: 549–557

Männikkö, M., Kestilä, M., Holmberg, C., Norio, R., Ryynänen, M., Olsen, A., Peltonen, L. and Tryggvason, K. (1995) Fine mapping and haplotype analysis of the locus for congenital nephrotic syndrome on chromosome 19q13.1. Am. J. Hum. Genet. 57: 1377–1383

Männikkö, Kestilä, M., Lenkkeri, U., Alakurtti, H., Holmberg, C., Leisti, J., Salonen, R., Aula, P., Mustonen, A., Peltonen, L. and Tryggvason, K. (1997) Improved prenatal diagnosis of the congenital nephrotic syndrome of the Finnish type nased on DNA analysis, Kidney Int. 51: 868–872

Martin, P., Heiskari, N., Hertz, J.-M-, Atkin, C., Barker, D., et al. Survey of mutations in the COL4A5 collagen gene in patients with suspected Alport syndrome: PCR amplification and direct sequencing of all 51 exon regions reveals over 80 mutation detection rate. (manuscript)

Noonan, D. M., Fulle, A., Valente, P., Cai, S., Horigan, E., Sasaki, M., Yamada, Y., and Hassell, J. R. (1991) The complete sequence of perlecan, a basement membrane heparan sulfate proteoglycan, reveals extensive similarity with laminin A chain, low density lipoprotein receptor, and the neural cell adhesion molecule. J. Biol. Chem. 266, 22939–22947

Norio, R. (1966) Heredity on the congenital nephrotic syndrome. Ann. Paediatr. Fenn. 12 (suppl 27):1–94

Olsen, A., Georgescu, A., Johnson, S. and Carrano, A. V. (1996) Assembly of a 1-Mb restriction-mapped cosmid contig spanning the candidate region for Finnish congenital nephrosis (NPHS1) in 19q13.1. Genomics 34:223–225

Pesheva, P., Gennarini, G., Goridis, C., and Schacher, M. (1993) The F3/11 cell adhesion molecule mediates the repulsion of neurons by the extracellular matrix glycoprotein J1-160/180. Neuron 10, 69–82

Pekkarinen P., Kestilä M., Hakola P., Järvi O., Tryggvason, K. and Palotie L. Fine-scale mapping of the PLO-SL locus. (manuscript)

Rapola, J., Huttunen, N. P. and Hallman, N. (1992) Congenital and infantile nephrotic syndrome. In: Edelman CM (ed.) Pediatric Kidney Disease. 2nd ed. Little, Brown and Company, Boston. Vol 2: 1291–1305

Renieri, A., Bruttini, M., Galli, L., Zanelli, P., Neri, T., et al. (1996) X-linked Alport syndrome: an SSCP-based mutation survey over all 51 exons of the COL4A5 gene. Am. J. Hum. Genet. 58, 1192–1204 Solovyev, V. V., Salamov, A. A., Lawrence, C. B. (1994) Predicting internal exons by oligonucleotide composition and discriminant analysis of spliceable open reading frames. Nucl. Acids Res. 22(24): 5156–5163

Tryggvason, K. (1996) Mutations in type IV collagen genes in Alport syndrome. In: Molecular pathology and Genetics of Alport syndrome (ed. K. Tryggvason). Contrib. Nephrol., 117, 154–171, Karger, Basel Tryggvason, K. and Kouvalainen, K. (1975) Number of nephrons in normal human kidneys and kidneys of patients with the congenital nephrofic syndrome. Nephron 15: 62–68

Uberbacher, E. C. and Mural, R. J. (1991) Locating protein-coding regions in human DNA sequences by a multiple sensor-neural network approach, Proc. Natl Acad. Sci. USA 88: 11261–11265

Zisch, A. H., D'Allessandri, L., Ranscht, B., Falchetto, R., Winterhalter, K. H., and Vaughan, L. (1992) Neuronal cell adhesion molecule contactin/F11 binds to tenascin via its immunoglobulin-like domains. J. Cell Biol. 119, 203–213

We claim:

1. An isolated nucleic acid comprising the nucleic acid sequence of SEQ ID NO: 1.

2. An expression vector containing the nucleic acid of claim 1.

3. An expression vector of claim 2 wherein said nucleic acid contains at least one intron.

4. A method for detecting the presence of the nucleic acid of claim 1 by contacting a cell sample with at least one nucleic acid probe which is specific for said nucleic acid and monitoring said sample for the presence of said nucleic acid.

* * * * *